United States Patent
Nussbaum et al.

(10) Patent No.: US 11,299,740 B2
(45) Date of Patent: Apr. 12, 2022

(54) ARTIFICIAL CHEMICAL ENTITY COMPRISING A DNA OLIGONUCLEOTIDE APTAMER THAT SELECTIVELY BINDS MUC1 ANTIGEN

(71) Applicants: Ofer Nussbaum, Rehovot (IL); Boaz Musafia, Hod Hasharon (IL)

(72) Inventors: Ofer Nussbaum, Rehovot (IL); Boaz Musafia, Hod Hasharon (IL)

( * ) Notice: Subject to any disclaimer, the term of this patent is extended or adjusted under 35 U.S.C. 154(b) by 209 days.

(21) Appl. No.: 16/476,297

(22) PCT Filed: Jan. 29, 2018

(86) PCT No.: PCT/IB2018/050524
§ 371 (c)(1),
(2) Date: Jul. 7, 2019

(87) PCT Pub. No.: WO2018/138695
PCT Pub. Date: Aug. 2, 2018

(65) Prior Publication Data
US 2019/0352642 A1 Nov. 21, 2019

Related U.S. Application Data

(60) Provisional application No. 62/499,536, filed on Jan. 30, 2017.

(51) Int. Cl.
| | | |
|---|---|---|
| *C12N 15/115* | (2010.01) | |
| *A61K 47/54* | (2017.01) | |
| *A61P 37/06* | (2006.01) | |
| *A61P 37/08* | (2006.01) | |
| *A61P 35/00* | (2006.01) | |
| *A61P 31/14* | (2006.01) | |
| *A61P 31/18* | (2006.01) | |
| *C07K 16/22* | (2006.01) | |

(52) U.S. Cl.
CPC .......... *C12N 15/115* (2013.01); *A61K 47/549* (2017.08); *A61P 31/14* (2018.01); *A61P 31/18* (2018.01); *A61P 35/00* (2018.01); *A61P 37/06* (2018.01); *A61P 37/08* (2018.01); *C07K 16/22* (2013.01); *C07K 2317/21* (2013.01); *C07K 2317/32* (2013.01); *C07K 2317/732* (2013.01); *C07K 2317/734* (2013.01); *C12N 2310/16* (2013.01); *C12N 2310/3513* (2013.01); *C12N 2310/3519* (2013.01)

(58) Field of Classification Search
CPC .............. C12N 15/115; C12N 2310/16; C12N 2310/3513; C12N 2310/3519; A61K 47/549; A61P 37/06; A61P 37/08; A61P 31/14; A61P 31/18; A61P 35/00; C07K 16/22; C07K 2317/21; C07K 2317/32; C07K 2317/732; C07K 2317/734
See application file for complete search history.

(56) References Cited

U.S. PATENT DOCUMENTS

| | | |
|---|---|---|
| 2005/0191680 A1 | 9/2005 | Bruno et al. |
| 2009/0018093 A1 | 1/2009 | Cload et al. |
| 2011/0275702 A1 | 10/2011 | Chang et al. |

FOREIGN PATENT DOCUMENTS

| | | |
|---|---|---|
| JP | 2016-088906 A | 5/2016 |
| KR | 2015-0115244 A | 10/2015 |
| WO | 2016/054107 A1 | 7/2016 |

OTHER PUBLICATIONS

Bruno, J.G., 2013. A review of therapeutic aptamer conjugates with emphasis on new approaches. Pharmaceuticals, 6(3), pp. 340-357.
International Search Report and Written Opinion for International Application PCT/IB2008/050524, dated Apr. 30, 2018.
Bruno, John G., Maria P. Carrillo, and Randy Crowell. "Preliminary development of DNA aptamer-Fc conjugate opsonins." Journal of Biomedical Materials Research Part A 90.4 (2009): 1152-1161. DOI: 10.1002/jbm.a.32182.
Dickgiesser, Stephan, et al. "Self-assembled hybrid aptamer-Fc conjugates for targeted delivery: a modular chemoenzymatic approach." ACS chemical biology 10.9 (2015): 2158-2165. DOI: 10.1021/acschembio.5b00315.
Bruno, John Gordon. "Aptamer -biotin -streptavidin -C1q complexes can trigger the classical complement pathway to kill cancer cells." In Vitro Cellular & Developmental Biology-Animal 46.2 (2010): 107-113. doi.org/10.1007/s11626-009-9257-7.
Stecker, John R., et al. "Dynamics and visualization of MCF7 adenocarcinoma cell death by aptamer-C1q-mediated membrane attack." Nucleic acid therapeutics 22.4 (2012): 275-282. DOI: 10.1089/nat.2012.0355.
Chawita et al 2013, "Synthetically modifed Fc domains as building blocks for immunotherapy applications" in Chemical Science, 4(1), 266-272.
Rader 2014, "Chemically Programmed Antibodies" in Trends in Biotechnology, 32(4), 186-197.
Kristian et al 2015, "Retargeting pre-existing human antibodies to a bacterial pathogen with an alpha-Gal conjugated aptamer" in J Molecular Medicine 93(6), 619-631.
Pollet et al 2012, "A peroxidase-active aptazyme as an isothermally amplifiable label in an aptazyme-linked oligonucleotide assay for low-picomolar IgE detection" in Analyst, 137(24), 5710.
Zhiyong Suo et al 2007, "Porphyrin as an Ideal Biomarker in the Search for Extraterrestrial Life" in Astrobiology 7(4), 605-615.
Boltz et al 2011, "Bi-specific Aptamers Mediating Tumor Cell Lysis" in J Biological Chemistry 286(24), 21896-21905.
Jun Ma et al 2013, "Target replacement strategy for selection of DNA aptamers against the Fc region of mouse IgG" in Genetics and Molecular Research 12(2), 1399-1410.
Nezlin 2016, "Use of aptamers in immunoassays" in Molecular Immunology 70, 149-154.
Extended EPO search report dated Oct. 5, 2020 for EP3574098, the publication of the EPO application corresponding to U.S. Appl. No. 16/476,297.
Branka Petricevic et al 2013 "Trastuzumab mediates antibody-dependent cell-mediated cytotoxicity and phagocytosis to the same extent . . . " in J Translational Medicine 11(307).

*Primary Examiner* — Robert S Landsman
(74) *Attorney, Agent, or Firm* — JMB Davis Ben-David

(57) ABSTRACT

Disclosed are artificial chemical entities, pharmaceutical compositions comprising such chemical entities and methods using the chemical entities. In some embodiments, the artificial chemical entity comprises a biomarker-bonding portion that selectively binds to a specified biomarker and an immune-response trigger that under in vivo conditions leads to positioning of an antibody Fc region in proximity of the biomarker to which the biomarker-bonding portion is bound.

10 Claims, 11 Drawing Sheets

Specification includes a Sequence Listing.

SEQUENCE LISTING

```
<160> NUMBER OF SEQ ID NOS: 8

<210> SEQ ID NO 1
<211> LENGTH: 43
<212> TYPE: DNA
<213> ORGANISM: Artificial Sequence
<220> FEATURE:
<223> OTHER INFORMATION: DNA aptamer
<220> FEATURE:
<221> NAME/KEY: n
<222> LOCATION: (1)..(1)
<223> OTHER INFORMATION: n is thiol-hexaethylene glycol
<220> FEATURE:
<221> NAME/KEY: misc_feature
<222> LOCATION: (1)..(1)
<223> OTHER INFORMATION: n is thiol-hexaethylene glycol
<300> PUBLICATION INFORMATION:
<301> AUTHORS: Dinh T. Tran, Kris P. F. Janssen, Jeroen Pollet, Elke
      Lammertyn, Jozef Ann, Ann Van Schepdael, Jeroen Lammertyn
<302> TITLE: Selection and Characterization of DNA Aptamers for Egg
      White Lysozyme
<303> JOURNAL: Molecules
<304> VOLUME: 15
<306> PAGES: 1127-1140
<307> DATE: 2010
<313> RELEVANT RESIDUES IN SEQ ID NO: (2)..(43)
```

<400> SEQUENCE: 1
natctacgaa ttcatcaggg ctaaagagtg cagagttact tag          43

<210> SEQ ID NO 2
<211> LENGTH: 47
<212> TYPE: DNA
<213> ORGANISM: Artificial Sequence
<220> FEATURE:
<223> OTHER INFORMATION: DNA Aptamer
<220> FEATURE:
<221> NAME/KEY: n
<222> LOCATION: (1)..(1)
<223> OTHER INFORMATION: n is thiol-hexaethylene glycol
<220> FEATURE:
<221> NAME/KEY: misc_feature
<222> LOCATION: (1)..(1)
<223> OTHER INFORMATION: n is thiol-hexaethylene glycol
<300> PUBLICATION INFORMATION:
<301> AUTHORS: Yong Huang, Xin-Min Ni, Shao-Long Gan, Jian-Hui Jiang ,
      Guo-Li Shen, Ru-Qin Yu
<302> TITLE: Electrochemical immunosensor of platelet-derived growth
      factor with aptamer-primed polymerase amplification
<303> JOURNAL: Analytical Biochemistry
<304> VOLUME: 382
<305> ISSUE: 1
<306> PAGES: 16-22
<307> DATE: 2008-11-01
<313> RELEVANT RESIDUES IN SEQ ID NO: (2)..(47)

<400> SEQUENCE: 2
ngcgatactc cacaggctac ggcacgtaga gcatcaccat gatcctg        47

<210> SEQ ID NO 3
<211> LENGTH: 71
<212> TYPE: DNA
<213> ORGANISM: Artificial Sequence
<220> FEATURE:
<223> OTHER INFORMATION: DNA aptamer
<220> FEATURE:
<221> NAME/KEY: n
<222> LOCATION: (1)..(1)
<223> OTHER INFORMATION: n is thiol-hexaethylene glycol
<220> FEATURE:
<221> NAME/KEY: misc_feature
<222> LOCATION: (1)..(1)
<223> OTHER INFORMATION: n is thiol-hexaethylene glycol
<300> PUBLICATION INFORMATION:
<301> AUTHORS: Catia S. M. Ferreira, Melissa C. Cheung, Sotiris
      Missailidis, Stuart Bisland, Jean Gariepy
<302> TITLE: Phototoxic aptamers selectively enter and kill epithelial
      cancer cells
<303> JOURNAL: Nucleic Acids Res
<304> VOLUME: 37
<305> ISSUE: 3
<306> PAGES: 866-876
<307> DATE: 2009
<313> RELEVANT RESIDUES IN SEQ ID NO: (2)..(71)

<400> SEQUENCE: 3
ngagacaaga ataaacgctc aagaagtgaa aatgacagaa cacaacattc gacaggaggc    60
tcacaacagg c                                                        71

<210> SEQ ID NO 4
<211> LENGTH: 71
<212> TYPE: DNA
<213> ORGANISM: Artificial Sequence
<220> FEATURE:
<223> OTHER INFORMATION: DNA aptamer
<220> FEATURE:
<221> NAME/KEY: n
<222> LOCATION: (1)..(1)
<223> OTHER INFORMATION: n is thiol-hexaethylene glycol

```
<220> FEATURE:
<221> NAME/KEY: misc_feature
<222> LOCATION: (1)..(1)
<223> OTHER INFORMATION: n is thiol-hexaethylene glycol
<300> PUBLICATION INFORMATION:
<301> AUTHORS: Catia S. M. Ferreira, Melissa C. Cheung, Sotiris
      Missailidis, Stuart Bisland, Jean Gariepy
<302> TITLE: Phototoxic aptamers selectively enter and kill epithelial
      cancer cells
<303> JOURNAL: Nucleic Acids Res
<304> VOLUME: 37
<305> ISSUE: 3
<306> PAGES: 866-876
<307> DATE: 2009
<313> RELEVANT RESIDUES IN SEQ ID NO: (2)..(71)

<400> SEQUENCE: 4
ngagacaaga ataaacgctc aaggctatag cacatgggta aaacgacttc gacaggaggc      60
tcacaacagg c                                                          71

<210> SEQ ID NO 5
<211> LENGTH: 25
<212> TYPE: DNA
<213> ORGANISM: Artificial Sequence
<220> FEATURE:
<223> OTHER INFORMATION: DNA aptamer
<300> PUBLICATION INFORMATION:
<301> AUTHORS: Catia S. M. Ferreira, Melissa C. Cheung, Sotiris
      Missailidis, Stuart Bisland, Jean Gariepy
<302> TITLE: Phototoxic aptamers selectively enter and kill epithelial
      cancer cells
<303> JOURNAL: Nucleic Acids Res
<304> VOLUME: 37
<305> ISSUE: 3
<306> PAGES: 866-876
<307> DATE: 2009
<313> RELEVANT RESIDUES IN SEQ ID NO: (1)..(25)

<400> SEQUENCE: 5
tggtggatgg cgcagtcggc gacaa                                           25

<210> SEQ ID NO 6
<211> LENGTH: 134
<212> TYPE: DNA
<213> ORGANISM: Artificial Sequence
<220> FEATURE:
<223> OTHER INFORMATION: DNA Aptamer with linker
<220> FEATURE:
<221> NAME/KEY: n
<222> LOCATION: (71)..(89)
<223> OTHER INFORMATION: n is deoxyribose 5-phosphate
<220> FEATURE:
<221> NAME/KEY: misc_feature
<222> LOCATION: (71)..(89)
<223> OTHER INFORMATION: n is deoxyribose 5-phosphate

<400> SEQUENCE: 6
gagacaagaa taaacgctca agaagtgaaa atgacagaac acaacattcg acaggaggct      60
cacaacaggc nnnnnnnnnn nnnnnnnngc gatactccac aggctacggc acgtagagca    120
tcaccatgat cctg                                                      134

<210> SEQ ID NO 7
<211> LENGTH: 134
<212> TYPE: DNA
<213> ORGANISM: Artificial Sequence
<220> FEATURE:
<223> OTHER INFORMATION: DNA aptamer with linker
```

```
<220> FEATURE:
<221> NAME/KEY: n
<222> LOCATION: (71)..(89)
<223> OTHER INFORMATION: n is deoxyribose 5-phosphate
<220> FEATURE:
<221> NAME/KEY: misc_feature
<222> LOCATION: (71)..(89)
<223> OTHER INFORMATION: n is deoxyribose 5-phosphate

<400> SEQUENCE: 7
gagacaagaa taaacgctca aggctatagc acatgggtaa aacgacttcg acaggaggct      60
cacaacaggc nnnnnnnnnn nnnnnnnngc gatactccac aggctacggc acgtagagca     120
tcaccatgat cctg                                                      134

<210> SEQ ID NO 8
<211> LENGTH: 113
<212> TYPE: DNA
<213> ORGANISM: Artificial Sequence
<220> FEATURE:
<223> OTHER INFORMATION: DNA aptamer with linker
<220> FEATURE:
<221> NAME/KEY: n
<222> LOCATION: (71)..(89)
<223> OTHER INFORMATION: n is deoxyribose 5-phosphate
<220> FEATURE:
<221> NAME/KEY: misc_feature
<222> LOCATION: (71)..(89)
<223> OTHER INFORMATION: n is deoxyribose 5-phosphate

<400> SEQUENCE: 8
gagacaagaa taaacgctca aggctatagc acatgggtaa aacgacttcg acaggaggct      60
cacaacaggc nnnnnnnnnn nnnnnnnntg gtggatggcg cagtcggcga caa            113
```

ARTIFICIAL CHEMICAL ENTITY COMPRISING A DNA OLIGONUCLEOTIDE APTAMER THAT SELECTIVELY BINDS MUC1 ANTIGEN

RELATED APPLICATION

The present Applications gains priority from U.S. provisional patent application 62/499,536 filed 30 Jan. 2017, which is included by reference as if fully set-forth herein.

SEQUENCE LISTING

This application incorporates-by-reference amino acid sequences, which are present in the file named "DNA aptamer for patent Jan2018_ST25.txt", which is 5 kbytes in size, and which was created on 23 Jan. 2018, having an operating system compatibility with MS-Windows, and is submitted herewith.

FIELD AND BACKGROUND OF THE INVENTION

The invention, in some embodiments thereof, relates to the field of medical therapy and pharmaceuticals. More particularly, some embodiments relate to artificial chemical entities that comprise a biomarker-bonding portion that selectively binds to a specified biomarker; and an immune-response trigger that under in vivo conditions leads to positioning of an antibody Fc region in proximity of the biomarker to which the biomarker-bonding portion is bound.

Some embodiments of the teachings herein relate to the field of drug delivery for treatment of cancer, autoimmune and infectious diseases. Some embodiments of the teachings herein provide novel techniques for activating the natural immune system, and especially the complement system, to induce cell death in pathogenic situation. In some such embodiments, the immune system activation occurs by IgG or IgG-Fc fraction chemically connected to target-specific oligonucleotide aptamer strands (herein sometimes called AptuBodies).

The Immune System, Antibodies and Memory B Cells

The immune system is a network of cells, tissues, and organs that work together to defend the body against attacks by "foreign" invaders. One aspect of the immune system is the antibodies formation system. The antibodies can recognize and bind to an invader and works to carry it out of the circulation, inactivate its activity and stimulate the complement system to destroy the invader (ref. 1). The immune system is built in a way that it does not recognize the body-related antigens and therefore does not produce anti self-antibodies nor attacks and destroy the body tissues (ref. 2).

Immunity is mediated by the secretion of antibodies and defend the body against extracellular harmful antigens such as bacteria, viruses, toxins and others. When an antigen with multiple epitopes gains entry into the body, different clones of B cells recognize and produce antibodies against the different epitopes. The first exposure to an antigen, leads to the activation of naive B lymphocytes. These B cells differentiate into antibody-producing plasma cells and memory cells. The antibody-producing B-cells usually produce the Abs only as long as the antigen is in the system, and then being eliminated from the body. On the other hand, the memory B-cells can stay in the system for several years (refs. 3, 4). The memory B-cells carry monomeric IgM-like immunoglobulin surface receptors that can recognize and bind to the specific antigen the cell is targeted against. When the same antigen enters the body again, it binds the B-cell monomeric IgM-like immunoglobulin surface receptors, and trigger a mechanism that stimulate the B-cell to secrete the relevant antibodies, and to start multiply and produce antibody-producing B-cells (ref. 3,4).

The IgG structure and the IgG binding sites are described in detail in refs. 4-7. The Variable domain (V) of the light chain is carrying the antibody antigen binding site. Every memory B-cell carry and produce an antibody which is recognizes specific epitope of antigen. As there are many epitopes in an antigen, there are many different memory B cells and therefore antibodies (Abs) that can recognize it. The whole group of Abs directed against a specific antigen are called "polyclonal Abs", while the Abs produce by one type of memory B cell are called "monoclonal Abs" (mAbs). mAbs can be grown in-vitro by performing single cell cloning of immortalized memory B-cell (Hybridomas) (refs.4,5).

The C1 region of the light chain and the C2 region of the heavy chain contains species specific sequences, differing the Abs from one species to another. These are highly immunologic sequences and inducing anti species-Abs upon introduction to another species (ref. 6). Employing gene engineering, species-specific sequences can be replaced in cultured cells producing mAbs, and change the species of the Abs. Humanization of IgG is one of the common ways to prepare Abs as a biological drug for treatment of human diseases such as cancer (ref. 6,7,8).

The two carboxylic ends of the heavy chain create the Fc region, which responsible to complement and T-cell activation, and bind specifically to Protein-A/protein-G.

The proteolytic enzyme Papain, can cleave IgG Ab to three parts, The Fc region and the two Fab' regions (ref. 7).

The Complement System

The complement system is an important branch of the immune system, which allows the system to eliminate pathogens. Complement is classically activated by the presence of antibodies attached to antigens on cell surface. The classical pathway is commonly initiated by the formation of soluble antibody complexes bound to particulate antigen or antigenic targets on the surface of whole cells, like virus, prokaryote, or eukaryote cells and involves the binding and activation of serum components C1, C2, C3 and C4. Antigen/antibody complexes induce conformational changes within the Fc region of the IgG or IgM molecule, exposing a binding site for the C1 component. Upon binding, C1q then C1r undergo conformational changes, activating C1r protease, which cleaves C1s, forming an active enzyme (ref. 9, 10). The activated cascade is being terminates in elimination of an antibody-associate cell mainly via lysis and death of the cell (ref.10). Circulating serum associate complement regulators, such as C1-inhibitor prevent the killing of surrounding cells, making the complement a safe system for killing pathogens (ref. 10). Unlike the Abs, the complement is not species specific, and working in vitro, almost any complement will be bound to and being activated by any species relevant Abs.

Autoimmune Diseases

An autoimmune disorder is a condition that occurs when the immune system mistakenly attacks and destroys healthy body tissue. Normally the immune system's white blood cells help in protecting the body from harmful substances (antigens), such as bacteria, viruses, toxins, cancer cells and tissues from another person or species. The immune system produces antibodies that destroy these harmful substances (ref. 11). In patients with an autoimmune disorder, the immune system recognizes healthy body tissue as alien antigen. The result is an immune response that destroys normal body tissues. This response is a hypersensitivity reaction similar to the response in allergic condition, where the immune system reacts to an outside substance that it normally would ignore (ref. 2, 11).

Overall, autoimmune diseases are common, reaching over than 80 different types, affecting more than 23.5 million Americans. They are a leading cause of death and disability. Yet some autoimmune diseases are rare, while others, such as Hashimoto's disease, affect many people.

Most autoimmune diseases are caused by the immune system attacking organs of the body. Since some of these diseases have common mechanism of action their treatment is essentially the same. They are treated with IVIG, steroids, plasmapheresis or other cytotoxic and immunosuppressive treatments.

Cancer Markers and Ab for Cancer Treatment

Over the past 20 years, it has been found that cancer cells are changing their cell surface proteins expression, and numerous of membrane-associated proteins specific for cancer cells has been discovered. These specific antigens which are expressed on the tumor cells cell surface differ them from normal cell. Most of these proteins are expressed and displayed on other tissues, and therefore do not induce the immune system (ref. 8, 12).

However, these proteins are of great interest, particularly because they are rich in targets for antibodies and therefore can be used as biomarkers for early tumor diagnosis, prognosis and cancer treatment. The suitability of several membrane-associated proteins as targets for drugs or antibodies has already been tested in preclinical and clinical studies (ref. 13).

Antibody-based therapy for cancer has become established over the past 15 years and is now one of the most successful and important strategies for treating patients with hematological malignancies and solid tumors. As the cancer cell surface markers do not induce the body immune system, these antigens must be introduced to another species immune system, followed by the isolation of mAbs and the humanization of the IgG to avoid the development of Abs against the drug.

The selection and development of monoclonal antibodies (mAbs) to reagents for human use also involves the affinity and avidity of the antibodies, the choice of antibody construct, the therapeutic approach (such as signaling abrogation or immune effector function) and the need to critically examine the pharmacokinetic and pharmacodynamic properties of antibodies in early clinical trials (refs. 8,14,15). The success in the development of monoclonal antibody-based anti-cancer drugs rose from the advancements made in recombinant technologies and cell culture production.

These humanized mAbs, derived from the antibodies of mouse origin, while maintaining the exquisite specificity and affinity to the tumor antigens, have low immunogenicity and toxicity in human. Once the humanized antibodies are available, they can be applied in several principal forms for cancer therapy, for example: naked antibodies, drug- or toxin-conjugates, and radio-conjugates (refs. 8, 16).

The mechanisms of tumor cell killing by naked antibodies are outlined in reference 8. This cell killing can be summarized as being due to several mechanisms: direct action of the antibody, through receptor blockade or agonist activity, induction of apoptosis, or delivery of a drug or cytotoxic agent; immune-mediated cell killing mechanisms, including, complement-dependent cytotoxicity (CDC), antibody-dependent cellular cytotoxicity (ADCC) and regulation of T cell function; and specific effects of an antibody on tumor vasculature and stroma. The Fc function of antibodies is particularly important for mediating tumor cell killing through CDC and ADCC. All of these approaches have been successfully applied in the clinic (ref. 8).

Drug- or toxin conjugates mAbs have shown poor safety in-vivo, as the toxin was found to affect not only the target cells (refs. 8, 15). A number of antibodies have been approved for the treatment of cancer (ref. 8)

Aptamers

In the last 10 years there is a growing use of aptamers as artificial chemical antibodies. Aptamers are single-strand oligonucleotides or oligopeptides that are able to fold into defined tertiary structures to bind their targets with high specificities and affinities (refs. 17, 18). Targets for which aptamers have successfully been produced against include proteins and cells biomarkers (refs. 17, 18, 19).

Aptamers have been suggested as valuable alternatives to antibodies in bio-detection and diagnostic applications due to their ease of discovery, their stability, and robust methods for their chemical synthesis (ref. 20). Moreover, as oligonucleotide aptamers have relatively low immunogenicity there is a growing use of aptamers as therapeutic drugs (ref. 21). Single oligonucleotide aptamers or libraries of oligonucleotide aptamers are easily available from commercial sources (e.g., Ella Biotech GmbH, Martinsried, Germany or ATDBio Ltd., University of Southampton, United Kingdom).

Unlike antibodies, aptamers selection is done in-vitro, does not rely on the analyte immunity and do not rely on animal systems. After selection, aptamers are produced by chemical synthesis and purified to a very high degree by eliminating the batch-to-batch variation found when using antibodies. A number of aptamers has been successfully selected against several cancer-related proteins and some types of cancer cells. It was found that only a few aptamers, such as those against the prostate cancer cells and breast cancer cells, have been reported to be taken up by the cells without additional assistance. Most aptamers cannot internalize into cells, limiting their capability as anti-cancer drug carrier for targeted therapy (refs. 21, 22).

SUMMARY OF THE INVENTION

Some embodiments of the invention herein relate to artificial chemical entities, pharmaceutical compositions comprising such chemical entities, uses of such chemical entities and methods using the chemical entities. In some embodiments, aspects of the invention may be used for therapy of pathologies such as cancer, autoimmune diseases, allergies and infectious diseases. More particularly, in some embodiments the artificial chemical entities comprise two portions. A first portion is a biomarker-bonding portion that selectively binds to a specified biomarker. A second portion is an immune-response trigger that under in vivo conditions leads to positioning of an antibody Fc region in proximity of the biomarker to which the biomarker-bonding portion is bound. Without wishing to be held to any one theory, it is currently believed that the positioning of the antibody Fc region in proximity of the biomarker activates the complement system to eliminate a pathogenic or pathological entity associated with the biomarker. In such a way, it is believed that some embodiments of the teachings herein lead to targeted triggering of an immune response.

In preferred embodiments (in some instances called aptubodies herein) the biomarker-bonding portion of a chemical entity comprises an oligonucleotide aptamer strand that selectively binds to the specified biomarker.

Some embodiments of the invention describe a novel approach for the therapy of cancer, autoimmune disease, allergies and infectious diseases, by triggering the immune system, employing a chemical entity having a biomarker-bonding portion to bind to specific biomarkers found on a cell (dependent on the embodiment, a eukaryotic cell or a prokaryotic cell).

In some embodiments, the chemical entity comprises, as an immune-response trigger an h-IgG or h-IgG-Fc, bound to the biomarker-bonding portion configured to specifically bind to a biomarker such as an antigen on the surface of a target cell.

The idea of triggering of the immune system and especially of the complement system by the artificial chemical entities of the teachings herein such as AptuBodies is based on our previous finding, inconsistent to the concept that the antigen/antibody complexes induce conformational changes within the Fc region of the antibody molecule, exposing a binding site for the C1q component. We have previously found that chemical binding of antibodies to red blood cells (and cultured cells) induced complement activation and cell lysis, depending on the number of IgG molecules bound to cell surface, reaching 85%-95% hemolysis when 15000-20000 IgG molecules were covalently bound to one cell surface. This result indicates that having two Fc regions close enough, triggers complement C1q binding and complement cascade activation.

In humans, to avoid the recognition of the Antibody as an antigen, an h-IgG (or other human Ab that can activate the complement) should be used. This h-IgG can be collected from O negative blood donors or from the patient himself (Personalized medicine). In addition, the IgG can be a human mAb directed against a target that cannot be found normally in the human system, such as a toxin, like Ricin-A. A second option is to eliminate the antigen binding site of the h-IgG by the using only the Fc region of the IgG. The AptuBodies are species specific, as directed by the source of the IgG, employing human-IgG or h-IgG-Fc fragment for human patients or any other species specific Abs for the treatment of the correlated species.

The biomarker-bonding portion such as an oligonucleotide aptamer strand can be selected to recognize and bind different cell surface antigens, such as cancer markers, the idiotypes of immunoglobulins presented on the surface of memory B-cells (for autoimmune disease and allergies), infectious substance surface proteins (such as bacteria and viruses) and others. As the single strand nucleic acid aptamers have poor immunity, low immune response if any is expected to them in the system.

The biomarker-bonding portion (also called target binding element) is not limited to nucleic acid aptamer strands, and can also be any ligand to a specific cell surface target, such as, but not limited to, oligopeptide (amino acid aptamer strands), growth factor, MIP, small molecule and others, as long as that target binding element is relatively inerratic to the immune system.

According to an aspect of some embodiments of the present invention there is provided a novel therapeutic concept for the use of AptuBodies, for activating the immune system, and especially the complement system, to induce cell death, employing either a semi-synthetic antibody\aptamer complex (IgG/Fc-aptamer base); or Dual Aptamer Complex base, and any other aptamer base combination of which one aptamer is directed against an antigen on the target cells surface, and the second activate the immune system, especially the complement system.

In some embodiments, these AptuBodies acts as therapeutic drug for the treatment of, but not limited to, cancer cells (solid and circulating tumors and tumor cells), Autoimmune diseases, allergies and infectious diseases (bacteria and viruses as well as infected cells).

Without wishing to be held to any one theory, the mechanism of AptuBodies triggering the immune system, and especially the complement system, leading to the target cell death, is based on the finding that complement C1q factor binds and activates the complement cascade, by binding to the Fc reagent of more than one Ab molecule, without the need of Ab/Ag association induced Ab conformation change. This indicates that there is a need for relatively massive gathering of Ag on the cell surface, to allow enough number of antibodies or Ab-Fc fragments to bind the target cells.

In some embodiments, the AptuBodies comprise an Ab (antibody) or Ab fraction such as, but not limited to, IgG or IgG-Fc fragment, bound to a nucleic acid aptamer portion, directed against a biomarker such as an antigen on the surface of a target cell surface, or a Dual Aptamer Complex (DAC, an aptamer derivative which includes two nucleic acid parts: a first nucleic acid aptamer part directed to bind to a biomarker such as an antigen on the target cells surface and the other against circulating antibodies or C1q protein.

The AptuBodies are species-specific, as directed by the type of the IgG, employing human-IgG or h-IgG-Fc fragment for human patients or any other species specific Abs for the treatment of the correlated species. The Ab source can be from poly or mono clonal Abs, or drown from the patient (i.e., subject) himself (Personalized Medicine).

The nucleic acid aptamer can be composed of RNA or DNA or a mix of nucleic acid or modified nucleic acid. The aptamer is selected against its target employing SELEX method, or/and any other nucleic acid aptamers selection method. The AptuBodies target binding element is not limited to Aptamers, and can also be any ligand to a specific cell surface target, such as, but not limited to, oligo peptide (amino acid aptamers), growth factor, small molecule and others, as long as that target binding element is relatively inerratic to the immune system.

The "binder"/Ab coupling could be either by chemical binding employing linkers and cross linkers, or as associative coupling.

The target for cancer cells can be, but not limited to, cancer cell, cell surface markers.

The Target for autoimmune diseases (and allergies) can be, but not limited to, the antigen binding domain of the membrane immunoglobin on the surface of Memory B-cells.

One Target for infectious diseases can be, but not limited to, invader antigens on the surface of infected cells (such as HCV and HIV antigens expressed on the surface of infected cell). Another target for infectious diseases can be, but not limited to, antigens on the surface of the invader itself (Bacteria virus or other), using the AptuBody also as Passive Immunization.

According to an aspect of some embodiments of the invention, there is also provided a novel substance comprised of AptuBodies wherein more than one type of aptamer are included, such as aptamers directed against different epitopes of the target antigen, aptamers directed against different targets, RNA or DNA aptamers, aptamers with different sequences, etc.

According to an aspect of some embodiments of the invention, there is also provided the use of the AptuBodies described herein or the use of AptuBodies as described herein.

According to an aspect of some embodiments of the invention, there is also provided a method as described herein wherein the first binding agent and the second binding agent are each independently an antibody, a nucleic acid aptamer, an amino acid aptamer, a receptor ligand or a molecular imprinted polymer (MIP).

According to an aspect of some embodiments of the invention, there is also provided a method wherein the binding aptamer comprises a reactive group at the 3' and/or 5' termini.

A method according to claim 1, claim 2 and claim 3, wherein the reactive group is selected from the group consisting of $NH_2$, SH, COOH, $PO_4$, Tosyl, thiol, a photo-reactive group and a member of an affinity couple, with or without a spacer between the nucleic acid sequence and the reactive group.

A method according to claim 1 wherein the cell surface antigen is a protein, a polypeptide, an oligopeptide, a peptide, a glycopeptide, a ganglioside, a lipid, a phospholipid, a carbohydrate, or a small molecule.

In some embodiments, the antigen is a cancer marker.

In some embodiments, the antigen is an Ab idiotope.

In some embodiments, the antigen is a viral antigen.

In some embodiments, the antigen is a bacteria antigen.

In some embodiments, the antigen is a Protozoa or other parasite antigen.

In some embodiments, the antigen or biomarker is expressed on the surface of the host cells.

In some embodiments, the antibody or the Fc region-source is of any immunoglobulin subunit such as any IgG, IgA, IgE, IgD, IgM, which naturally or by modification can bind the complement antigens.

In some embodiments, the antibody or the Fc region source is of a poly clonal or a mono clonal, fully human or humanized, or derived from the patient (subject) himself.

In some embodiments, the antibody consists of an antibody of a human, a primate, a household animal and any other animal.

According to an aspect of some embodiments of the present invention, there is also provided an artificial chemical entity, comprising:
a. a biomarker-bonding portion that selectively binds to a specified biomarker; and
b. an immune-response trigger that under in vivo conditions leads to positioning of an antibody Fc region in proximity of the biomarker to which the biomarker-bonding portion is bound.

Without wishing to be held to any one theory, it is currently believed that if the cell has a sufficiently high expression of the biomarker (e.g., the cell is pathological or is a pathogenic cell to be treated), sufficient antibody Fc regions are positioned close enough together to activate the complement system to attack the cell with a membrane attack complex, thereby eliminating the cell.

In some embodiments, the specified biomarker is on the surface of a cell or virus envelope, and under in vivo conditions the immune-response trigger leads to positioning of an antibody Fc region in proximity of the surface.

In some embodiments, the biomarker-bonding portion comprises a chemical group selected from the group consisting of: an oligonucleotide that constitutes an oligonucleotide aptamer strand, an oligopeptide that constitutes a peptide aptamer strand, a ligand to the specified biomarker, a receptor ligand, a growth factor and a small molecule residue. In some embodiments, the biomarker-bonding portion consists of one chemical group selected from the group consisting of: an oligonucleotide that constitutes an oligonucleotide aptamer strand, an oligopeptide that constitutes a peptide aptamer strand, a ligand to the specified biomarker, a receptor ligand, a growth factor and a small molecule residue.

In some embodiments, the biomarker-bonding portion comprises an oligonucleotide aptamer strand that selectively binds to the specified biomarker.

In some embodiments, the biomarker-bonding portion is selected from the group consisting of a DNA strand, an RNA strand, a strand including both RNA and DNA, and a strand including a modified nucleic acid.

In some embodiments, the biomarker-bonding portion is not less than 15 nucleic acid residues long.

In some embodiments, the biomarker-bonding portion is not more than 80 nucleic acid residues long.

In some embodiments, the cell is selected from the group consisting of a pathogen, a pathological cell and a memory autoimmune cell.

In some embodiments, the biomarker is selected from the group consisting of: an antigen; and an entity expressed on the surface of the cell, the entity selected from the group consisting of a protein, a polypeptide, an oligopeptide, a peptide, a glycopeptide, a ganglioside, a lipid, a phospholipid, a carbohydrate and a small molecule.

In some embodiments, the biomarker is an antigen selected from the group consisting of a cancer marker, an Ab antigen binding site idiotope, a viral antigen, a bacteria antigen, a parasite antigen, a protozoa antigen and a prion.

In some embodiments, the biomarker-bonding portion is bonded to the immune-response trigger with a non-covalent associative bond.

In some embodiments, the biomarker-bonding portion is directly covalently bonded with a covalent bond to the immune-response trigger. In some embodiments, the biomarker-bonding portion comprises an oligonucleotide aptamer strand that selectively binds to the specified biomarker and wherein the covalent bond is through a 5' terminus of the oligonucleotide strand. In some embodiments, the biomarker-bonding portion comprises an oligonucleotide aptamer strand that selectively binds to the specified biomarker and wherein the covalent bond is through a 3' terminus of the oligonucleotide strand. In some embodiments, the covalent bond is through a residue of a reactive group selected from the group consisting of $NH_2$, SH, COOH, $PO_4$, Tosyl, thiol, a photo-reactive group and a member of an affinity couple.

In some embodiments, the chemical entity further comprises a linker bonded to the biomarker-bonding portion with a non-covalent associative bond.

In some embodiments, the chemical entity further comprises a linker covalently bonded with a covalent bond to the biomarker-bonding portion. In some embodiments, the biomarker-bonding portion comprises an oligonucleotide aptamer strand that selectively binds to the specified biomarker and wherein the covalent bond is through a 5' terminus of the oligonucleotide strand. In some embodiments, the biomarker-bonding portion comprises an oligonucleotide aptamer strand that selectively binds to the specified biomarker and wherein the covalent bond is through a 3' terminus of the oligonucleotide strand. In some embodiments, the covalent bond is through a residue of a reactive group selected from the group consisting of $NH_2$, SH, COOH, $PO_4$, tosyl, thiol, a photo-reactive group and a member of an affinity couple. In some embodiments, the immune-response trigger is bonded to the linker with a non-covalent associative bond. In some embodiments, the immune-response trigger is covalently bonded to the linker. In some embodiments, the linker is a chain comprising individual monomer residues selected from the group consisting of monosaccharide residues, nucleotide residues and combinations thereof. In some embodiments, the chain is linear. In some embodiments, the chain is not less than 3 monomer residues long. In some embodiments, the chain is not more than 50 monomer residues long.

In some embodiments, the immune-response trigger comprises an Fc portion of an antibody selected from the group consisting of IgG, IgA, IgE, IgD and IgM. In some embodiments, the immune-response trigger consists of an Fc portion of an antibody selected from the group consisting of IgG, IgA, IgE, IgD and IgM.

In some embodiments, the immune-response trigger comprises an antibody selected from the group consisting of IgG, IgA, IgE, IgD and IgM. In some embodiments, the immune-response trigger consists of an antibody selected from the group consisting of IgG, IgA, IgE, IgD and IgM.

In some embodiments, the antibody is selected from the group consisting of a polyclonal antibody, a monoclonal antibody and a humanized antibody.

In some embodiments, the antibody is of a species selected from the group consisting of: human, a non-human species of the order Primates, a species of the class Ayes (especially from the order of galliformes such as domestic chickens and turkeys), a species in the family bovidae (such as cattle, sheep, goats), a species in the family felidae (such as a domestic cat), and a species in the family canidae (such as a domestic dog).

In some embodiments, the immune-response trigger comprises an oligonucleotide aptamer strand that selectively binds to an antibody under in vivo conditions.

In some embodiments, the immune-response trigger oligonucleotide aptamer strand is selected from the group consisting of a DNA strand, an RNA strand, a strand including both RNA and DNA, and a strand including a modified nucleic acid.

In some embodiments, the antibody to which the immune-response trigger oligonucleotide aptamer strand selectively binds to under in vivo conditions is selected from the group consisting of IgG, IgA, IgE, IgD and IgM. In some embodiments, the in vivo conditions are in a human organism. In some embodiments, the in vivo conditions are in a non-human organism.

According to an aspect of some embodiments of the teachings herein, there is also provided an artificial chemical entity, comprising:
 a. a biomarker-bonding portion that selectively binds to a specified biomarker; and
 b. an immune-response trigger that under in vivo conditions leads to positioning of complement C1q protein in proximity of said biomarker to which said biomarker-bonding portion is bound.

According to an aspect of some embodiments of the present invention, there is also provided a chemical entity according to the teachings herein, for use in therapy of a pathological condition.

According to an aspect of some embodiments of the present invention, there is also provided the use of a chemical entity according to the teachings herein, for the preparation of a pharmaceutical composition for treating a pathological condition.

According to an aspect of some embodiments of the present invention, there is also provided a chemical entity according to the teachings herein, for use as a medicament for treating a pathological condition.

According to an aspect of some embodiments of the present invention, there is also provided a method of treatment, comprising administering a pharmaceutically-effective amount of a chemical entity according to the teachings herein to a subject in need thereof. According to an aspect of some embodiments of the present invention, there is also provided method of treatment of a pathological condition, comprising administering a pharmaceutically-effective amount of a chemical entity according to the teachings herein to a subject in need thereof. In some embodiments, the subject is a human. In some embodiments, the subject is a non-human animal. In some embodiments, the need is that the subject suffers from a pathological condition.

According to an aspect of some embodiments of the present invention, there is also provided a pharmaceutical composition comprising: a chemical entity according to the teachings herein; and a pharmaceutically-acceptable carrier, for the treatment of a pathological condition.

In some embodiments of the uses, methods or compositions, the pathological condition is selected from the group consisting of cancer, an autoimmune disease, an allergy and infectious diseases.

In some embodiments of the uses, methods or compositions, the pathological condition is cancer and wherein the biomarker-bonding portion is for selectively binding to a specified biomarker on the surface of a cancerous cell In some embodiments of the uses, methods or compositions, the pathological condition is selected from the group consisting of an autoimmune disease and an allergy and wherein the biomarker-bonding portion is for selectively binding to a target binding idiotope of a membrane immunoglobulin molecule on the surface of a memory B-cell.

In some embodiments of the uses, methods or compositions, the pathological condition is an infectious disease caused by a pathogen, and wherein the biomarker-bonding portion is for selectively binding to a specified biomarker on the surface of the pathogen cell. In some embodiments, the pathogen cell is selected from the group consisting of parasite, bacteria and protozoa. In some embodiments, the biomarker is an antigen.

In some embodiments of the uses, methods or compositions, the pathological condition is an infectious disease caused by a pathogen, and wherein the biomarker-bonding portion is for selectively binding to a specified biomarker on the surface of a cell infected by a pathogen. In some embodiments, the pathogen cell is selected from the group consisting of a bacterium and a virus. In some embodiments, the biomarker is an invader antigen.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the FIGS. are not to scale.

In the Figures:

FIG. 2A graphically depict a hypothetical mechanism by which a chemical entity according to the teachings herein triggers the complement system:

FIG. 2A-1 depicts how two different types of chemical entity according to the teachings herein,
a chemical entity 10 (in the depicted embodiment, comprising an oligonucleotide aptamer strand 12 as a biomarker-bonding portion and an IgG antibody 14 as an immune-response trigger) and
a chemical entity 16 (in the depicted embodiment, comprising an oligonucleotide aptamer strand 12 as a biomarker-bonding portion and a Fc portion of an IgG antibody 18 as an immune-response trigger)
bind with the biomarkers on the cell wall 36 of a cell 38 which has a low density of biomarkers: due to the low density of biomarkers, the number of chemical entities 10 or 16 is insufficient to activate the complement system against cell 38, In contrast, FIG. 2A-2 depicts how multiple chemical entities 10 or 16 bind with the biomarkers on the cell wall 36 of a cell 40 which has a high density of biomarkers: due to the high density of biomarkers, a number of chemical entities 10 or 16 that is sufficient to activate the complement system against cell 40, binds to the biomarkers on cell wall 36 of cell 40, leading to the death of cell 40;

FIG. 2B-1a depicts chemical entities according to the teachings herein 26 (as depicted in FIG. 1D) bonding to biomarkers 42 on cell wall 36 of a cell through a biomarker-bonding portion thereof and bonding to IgG antibodies 34 from the blood stream through an immune-response trigger portion thereof in sufficient density to activate the complement system via Complement C1q 44;

FIG. 2B-1b depicts a chemical entity according to the teachings herein 46 (substantially similar to 26, but with an oligonucleotide aptamer strand configured to selectively bind complement C1q as an immune-response trigger) bonding to a biomarker 42 on cell wall 36 of a cell through a biomarker-bonding portion thereof and bonding to a Complement C1q 44 from the blood stream through an immune-response trigger portion thereof, thereby activating the complement system by directly bonding to a Complement C1q 44 from the blood stream;

FIG. 2B-2 depicts treatment of an autoimmune disease by two chemical entities according to the teachings herein 26 (as depicted in FIG. 1D) bonding to biomarkers 42 (memory immunoglobulin) on cell wall 36 of a cell (a memory B cell) through a biomarker-bonding portion thereof, and bonding to IgG antibodies 34 from the blood stream through an immune-response trigger portion thereof in sufficient density to activate the complement system via Complement C1q 44;

and a chemical entity according to the teachings herein 46 (with an oligonucleotide aptamer strand configured to selectively bind complement C1q as an immune-response trigger) bonding to a biomarker 42 (memory immunoglobulin element) on cell wall 36 of a cell (a memory B cell) through a biomarker-bonding portion thereof, and bonding to a Complement C1q 44 from the blood stream through an immune-response trigger portion thereof thereby activating the complement system by directly bonding to a Complement C1q 44 from the blood stream.

Figure 4:
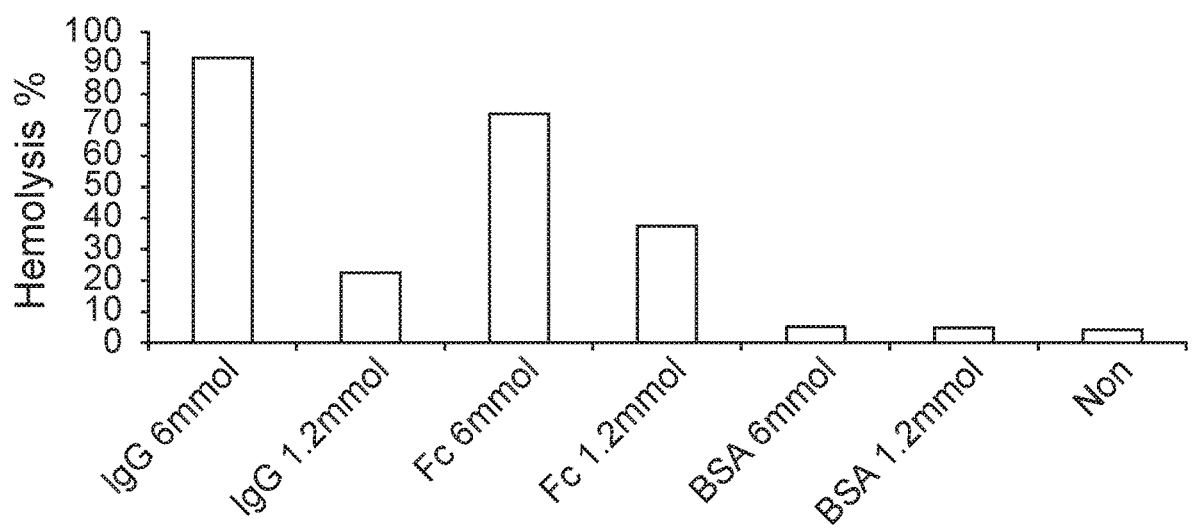
Figure 6:
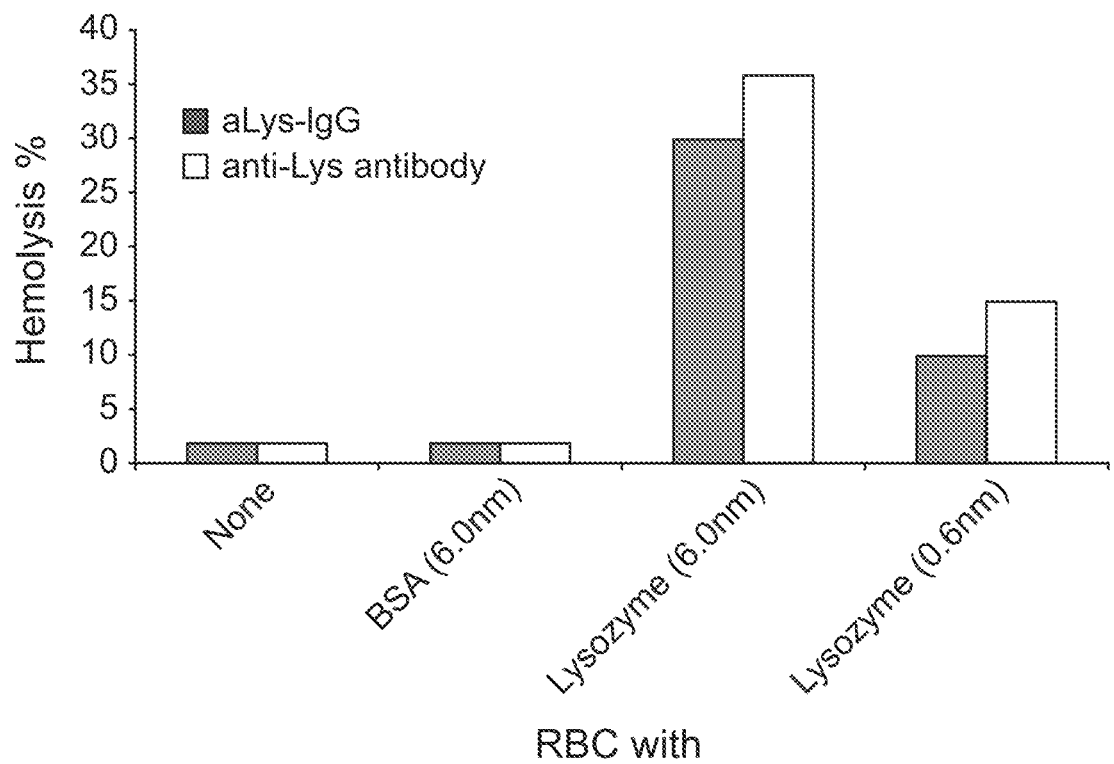
Figure 7:
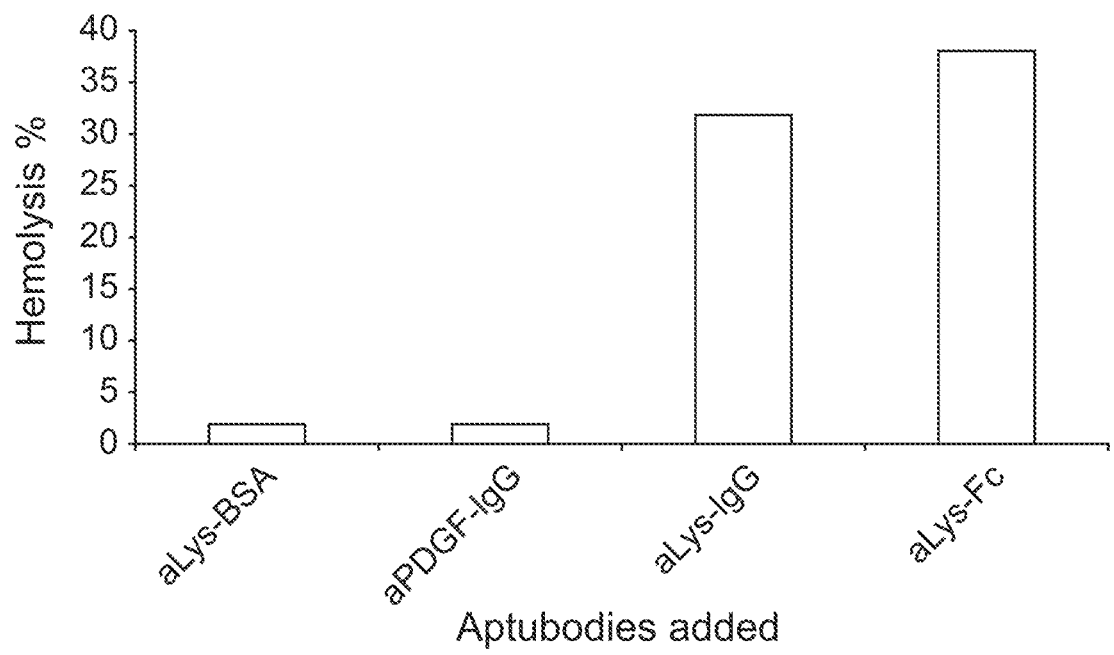
Figure 8:
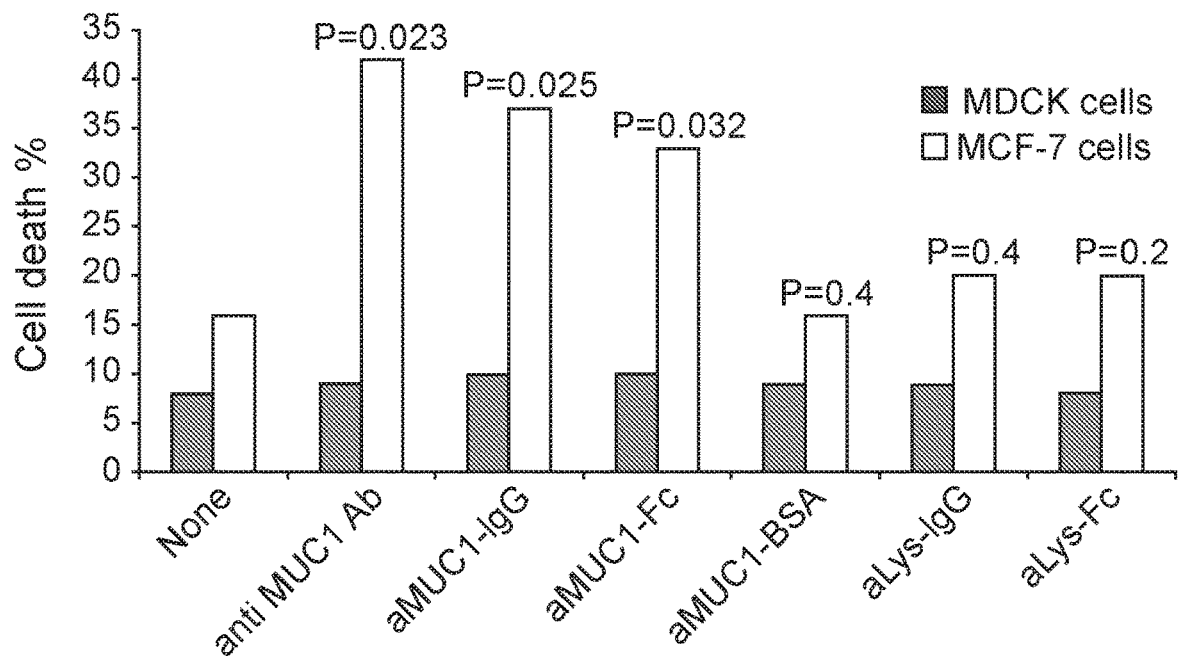
Figure 9:
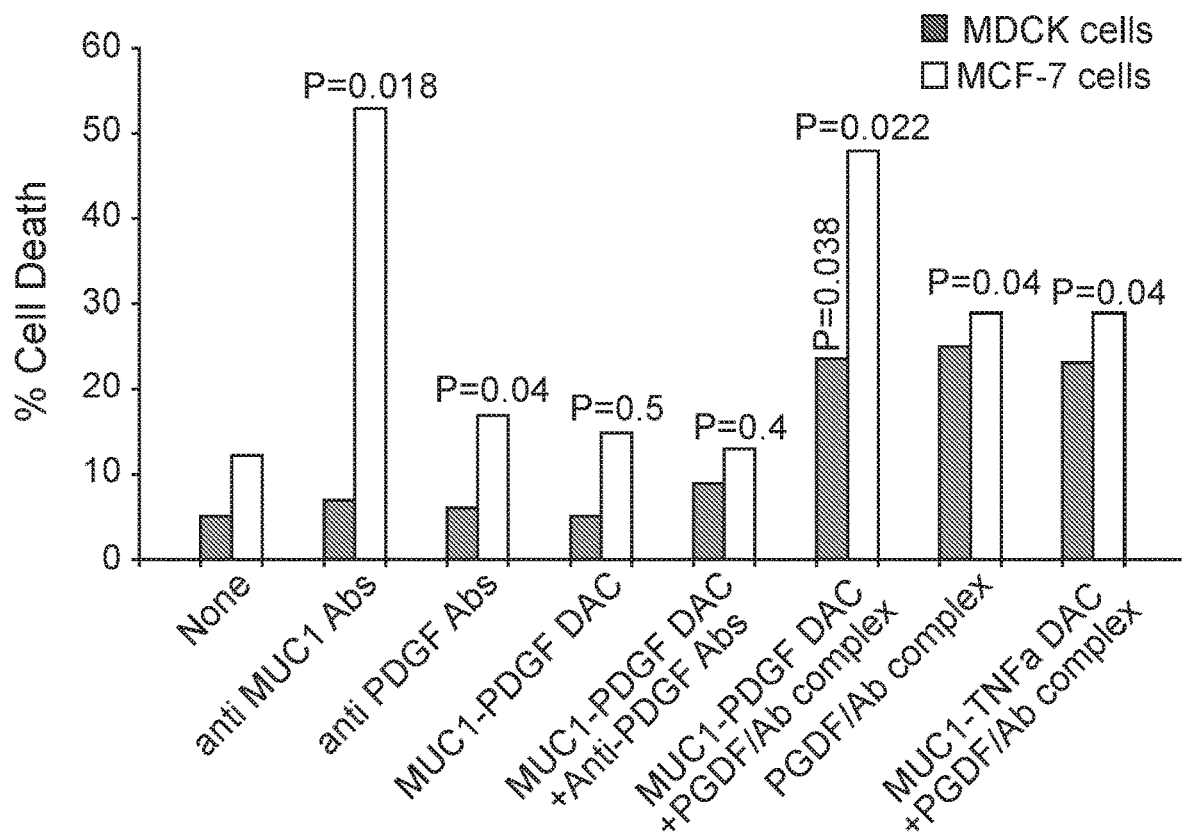
Figure 10:
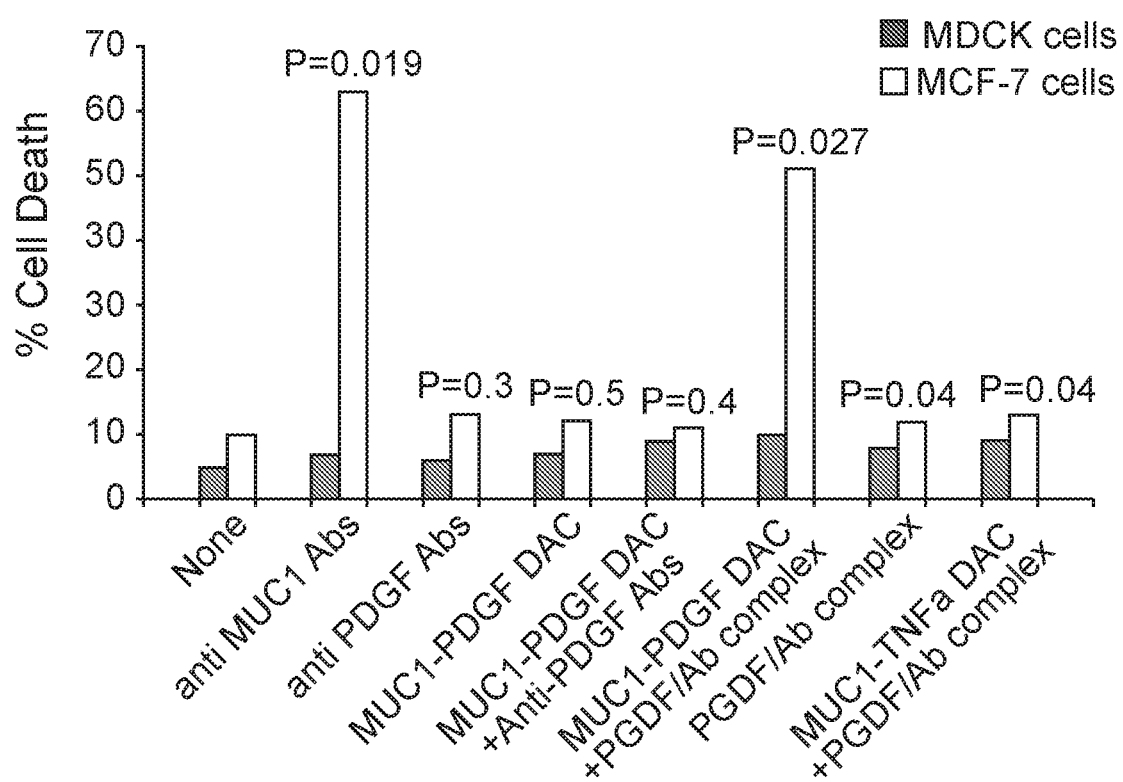

FIGS. 3A-3D are reproductions of photographs showing modified RBCs bound to Protein-A/Sepharose beads;

FIG. 4 graphically depicts experimental results showing complement-induced hemolysis of IgG/Fc coupled RBCs;

FIGS. 5A-5F are reproductions of photographs showing that embodiments of a chemical entity according to the teachings herein (called AptuBodies) induced agglutination of modified RBCs;

FIG. 6 graphically depicts experimental results showing that an embodiment of a chemical entity according to the teachings herein (called aLys-IgG) induces hemolysis of Lysozyme-RBC;

FIG. 7 graphically depicts experimental results showing that an embodiment of a chemical entity according to the teachings herein (called aLys-IgG) induces hemolysis of Lysozyme-RBC;

FIG. 8 graphically depicts experimental results showing that an embodiment of a chemical entity according to the teachings herein (called Aptubodies) induces cultured cell death;

FIG. 9 graphically depicts experimental results showing that an embodiment of a chemical entity according to the teachings herein (called DAC particles) induces cultured cell death; and FIG. 10 graphically depicts experimental results showing that an embodiment of a chemical entity according to the teachings herein (called DAC particles) induces cultured cell death.

DESCRIPTION OF SOME EMBODIMENTS OF THE INVENTION

Some embodiments of the teachings herein relate to artificial chemical entities, pharmaceutical compositions comprising such chemical entities, uses of such chemical entities and methods using the chemical entities. In some embodiments, aspects of the invention may be used for therapy of pathologies such as cancer, autoimmune diseases, allergies and infectious diseases. More particularly, in some embodiments the artificial chemical entities comprise two portions. A first portion is a biomarker-bonding portion that selectively binds to a specified biomarker. A second portion is an immune-response trigger that under in vivo conditions leads to positioning of an antibody Fc region in proximity of the biomarker to which the biomarker-bonding portion is bound.

The principal object of some embodiments of the teachings herein is the construction of a novel chemical entities called AptuBodies, for the therapy of cancer, autoimmune disease, allergies and infectious diseases, by activating the immune system.

An additional object of some embodiments of the teachings herein is to provide a general method for the construction and preparation of "AptuBodies" as a chimeric IgG/IgG-Fc which are bound to nucleic acid aptamers that acts as cell surface markers binding elements.

Another object of some embodiments of the teachings herein is to provide a new approach in the treatment of autoimmune disease and allergies, by specific eliminating the abnormal memory B-cells.

Another object of some embodiments of the teachings herein is to provide a tool for performing personalized medicine.

Methods and techniques for achieving these and other objects of the different embodiments of the teachings herein, are readily apparent to a person having ordinary skill in the art upon perusal of the specification.

Construction of Assay Components

Some embodiments of the teachings herein relate to a novel approach for the therapy of cancer, autoimmune disease, allergies and infectious diseases, by triggering the immune system, employing biomarker-bonding entities such as nucleic acid aptamers as biomarker binding elements and antibodies such as IgG as an element for triggering the immune-response system.

Some such antibody\aptamer complexes (AptuBodies) comprise h-IgG or h-IgG-Fc, bound to a specific nucleic acid aptamer strand, directed against a biomarker such as an antigen on the target cells surface.

In some such embodiments, the nucleic acid aptamer strand can be selected to recognize and bind different cell surface antigens, such as cancer markers, the idiotypes of membrane immunoglobins presented on the surface of memory B-cells (for autoimmune disease and allergies), infectious substance surface proteins (such as bacteria and viruses) and others. As the single strand nucleic acid aptamers have poor immunity, a low immune response is expected.

Depending on the embodiment, the antibody can be an h-IgG (or other human Ab that can activate the complement), or Fc region of the IgG, eliminating the IgG binding region idiotope. In some embodiments, preferably, the IgG or FC source is from human source, to avoid species-directed immunity. The IgG can also come from the patient himself (Personalized medicine), or as a human mAb directed against a target that cannot be found normally in the human system.

Figure 1A:
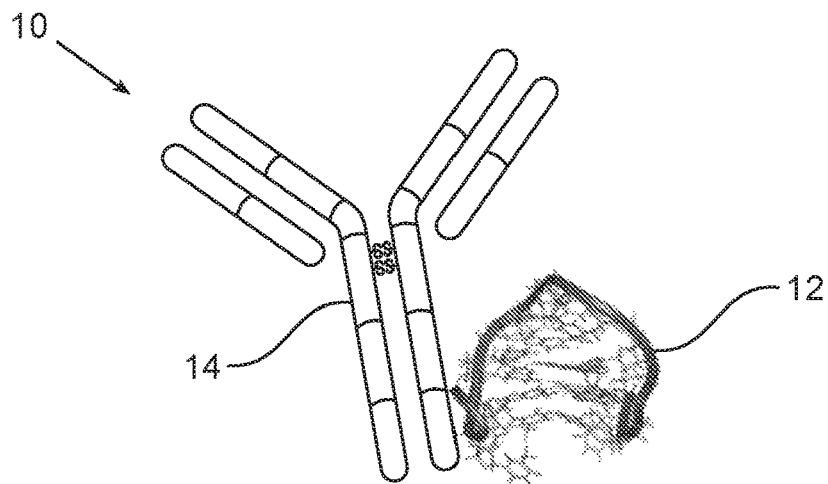
FIG. 1A schematically depicts an embodiment 10 of a chemical entity according to the teachings herein in which:
the biomarker-bonding portion is an oligonucleotide aptamer strand 12, and
the immune-response trigger consist of an IgG antibody 14,
wherein the biomarker-bonding portion 12 is bonded to the immune-response trigger 14 with a covalent bond.
Figure 1B:
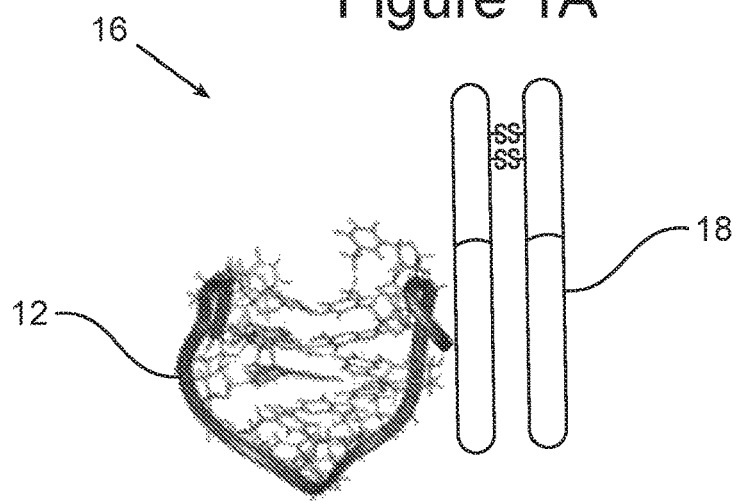
FIG. 1B schematically depicts an embodiment 16 of a chemical entity according to the teachings herein in which:
the biomarker-bonding portion is an oligonucleotide aptamer strand 12, and
the immune-response trigger consists of an Fc region 18 of an IgG antibody, wherein the biomarker-bonding portion 12 is bonded to the immune-response trigger 18 with a covalent bond.

Binding of an aptamer strand to a protein can be induced in several ways, such as chemical binding or association binding. An example to chemical binding, employing cross linkers, but not limited to, is a 5' or 3' thiol (SH) modified oligonucleotide aptamer can be covalently binds to maleimide modified protein. Any other chemistry that will not affect the Ab or Fc ability to bind and activate the complement can be used, see FIGS. 1A and 1B.

Figure 1C:
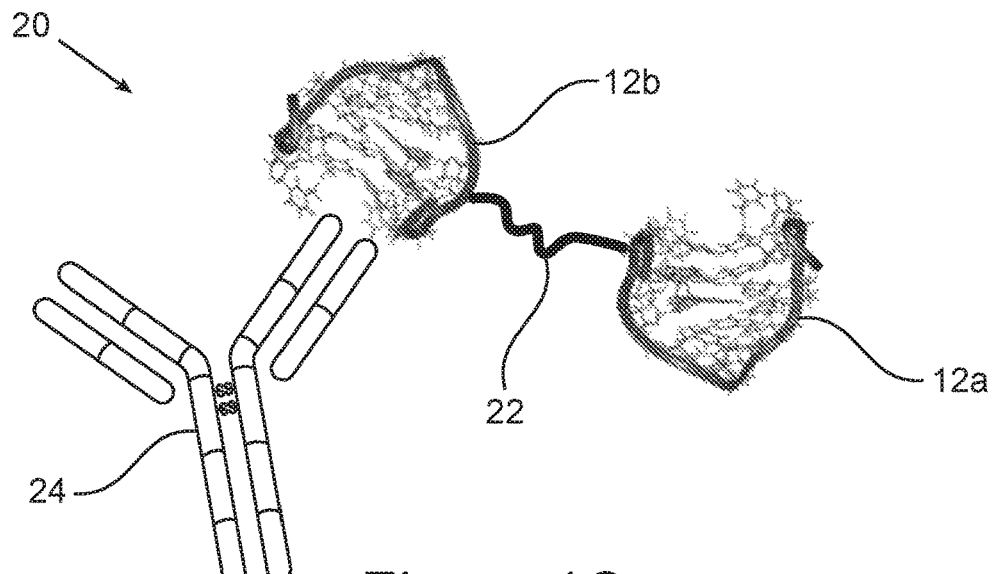
FIG. 1C schematically depicts an embodiment 20 of a chemical entity according to the teachings herein in which:
the biomarker-bonding portion is a first oligonucleotide aptamer strand 12a, and
the immune-response trigger is a second oligonucleotide aptamer strand 12b, wherein the biomarker-bonding portion 12a is bonded to the immune-response trigger 12b with a linker 22, where the immune-response trigger 12b is depicted bonded to an IgG antibody 24.

The use of linkers, such as PEG or others, between the Ab and the oligonucleotide aptamer is possible. An example to association binding, but not limited to, is the use of "fused" two aptamers, which one is directed against the chosen cell surface antigen and the other against the antigen binding site of a human mAb (such as mAb against Ricin-A). This will eliminate any potential steric interference for C1q binding to the Fc, see FIG. 1C.

Figure 1D:
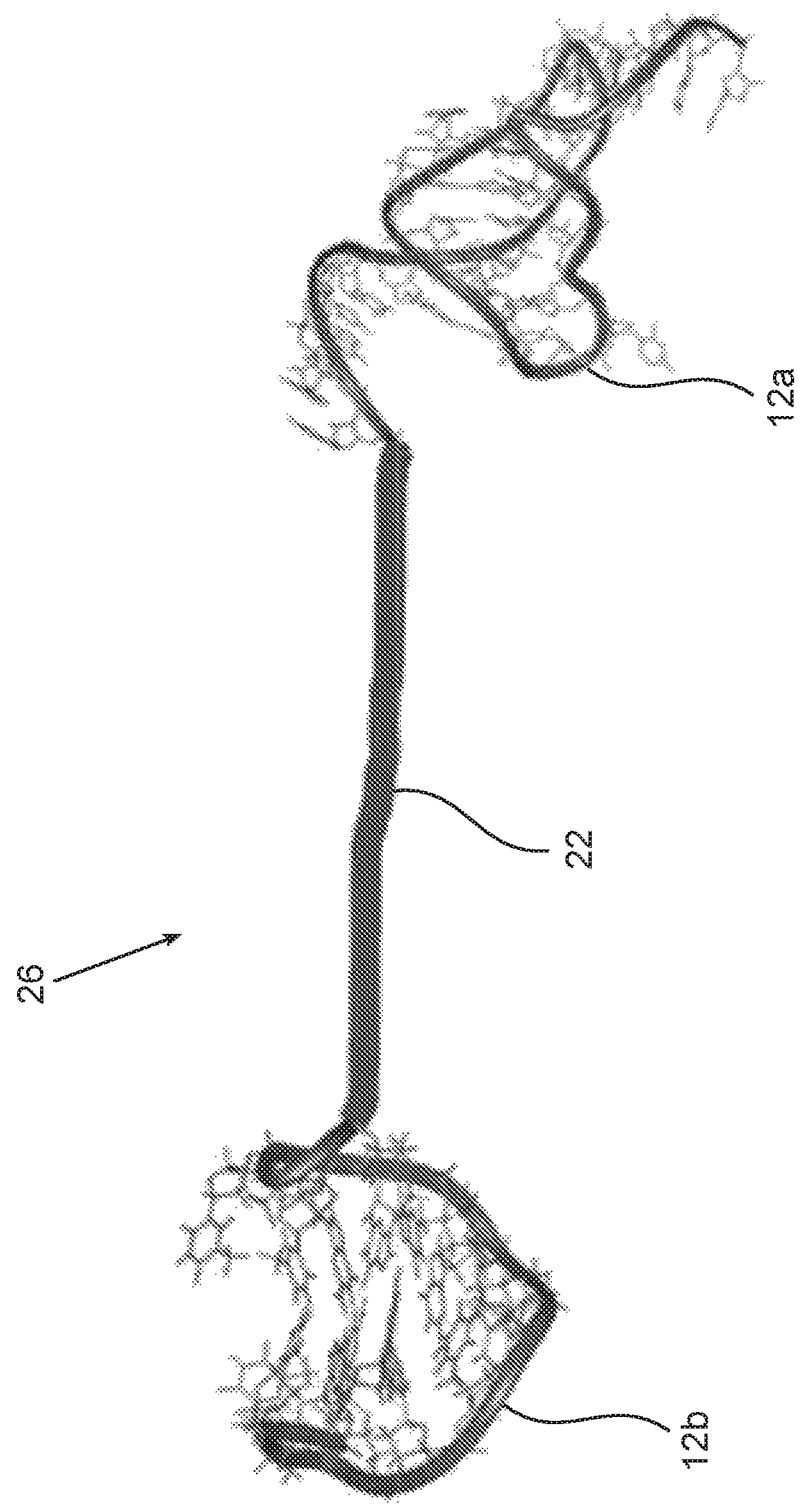
FIG. 1D schematically depicts an embodiment 26 of a chemical entity according to the teachings herein in which:
the biomarker-bonding portion is a first oligonucleotide aptamer strand 12a (e.g., biomarker on a cell surface, or a biomarker on cancer cell or immunoglobulin idiotope of autoimmune cell), and
the immune-response trigger is a second oligonucleotide aptamer strand 12b (e.g., to bond to h-IgG, complement C1q),
wherein the biomarker-bonding portion 12a is bonded to the immune-response trigger 12b with a linker 22 made up of either 2 or 3 Sp18 sublinkers, each Sp18 sublinker being a DNA skeleton of 18 sugar residues and phosphates, about 3.5-5.0 nm long.
wherein:
the 5' terminus of second oligonucleotide aptamer strand 12b is free,
the 3' terminus of second oligonucleotide aptamer strand 12b is covalently bonded to
the 5' terminus of linker 22,
the 3' terminus of linker 22 is covalently bonded to the 5' terminus of first oligonucleotide aptamer strand 12a, and
the 3' terminus of first oligonucleotide aptamer strand 12a is free and where the entire chemical entity 26 has an average molecular weight of 35000 Dalton.
Figures 1, 2A:
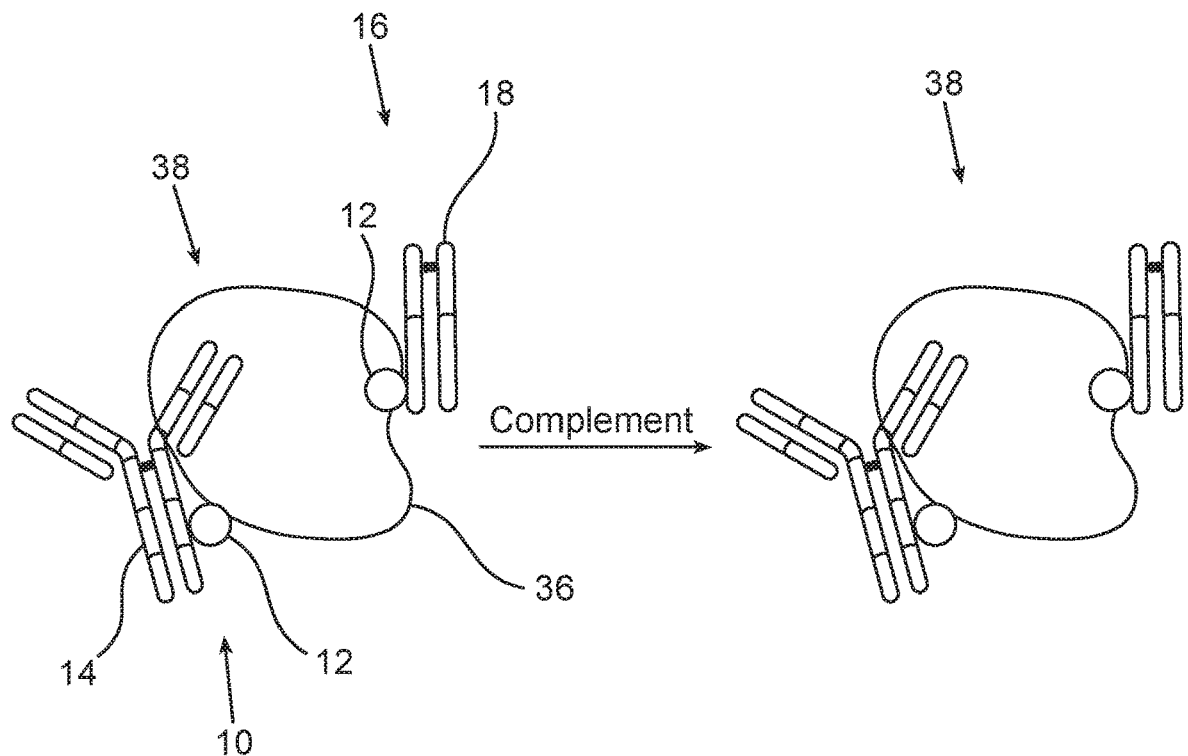
Figures 2, 2A:
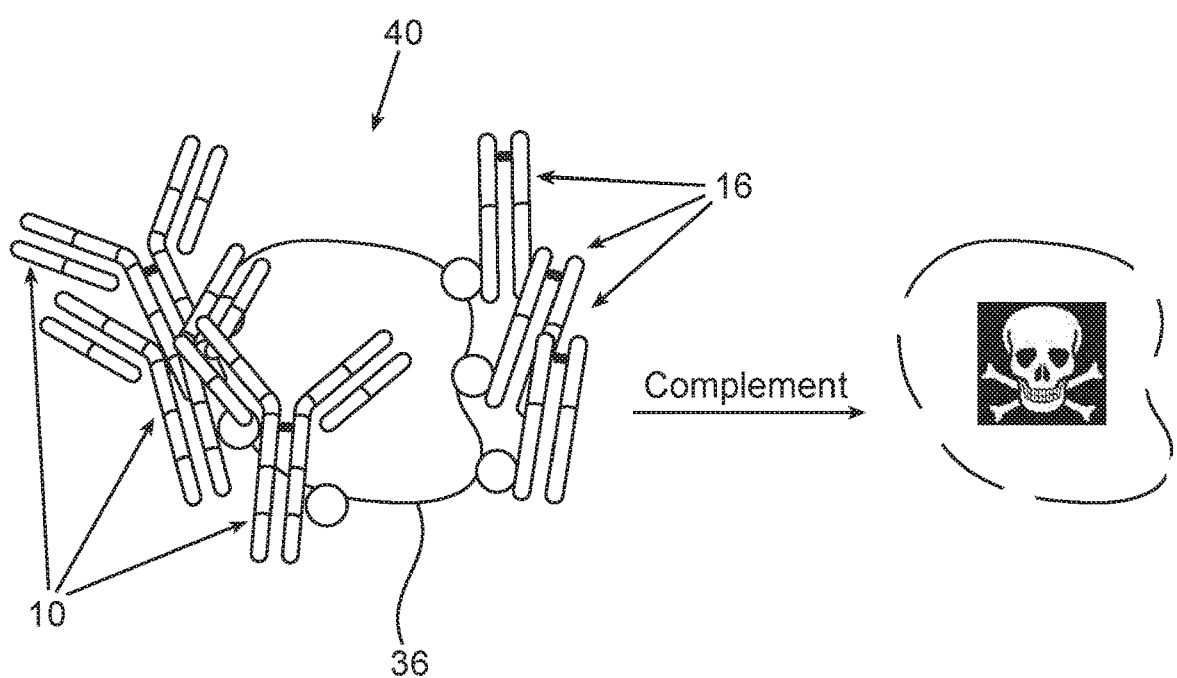
Figures 1B, 2B:
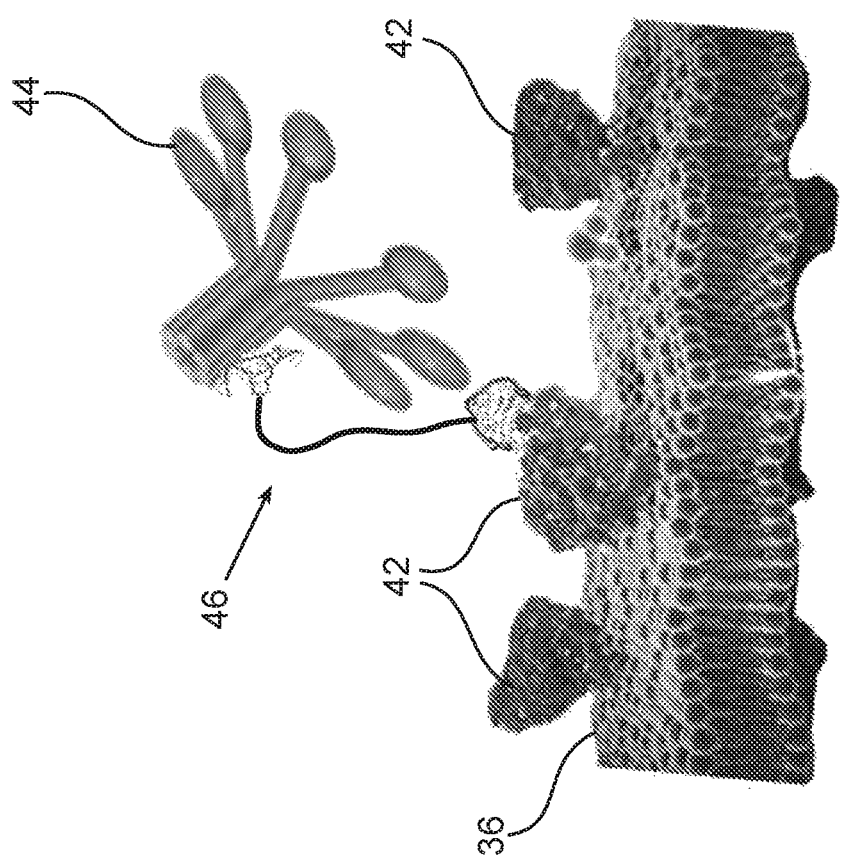
FIG. 2B graphically depicts a hypothetical mechanism by which a chemical entity according to the teachings herein triggers the complement system.
Figures 1A, 2B:
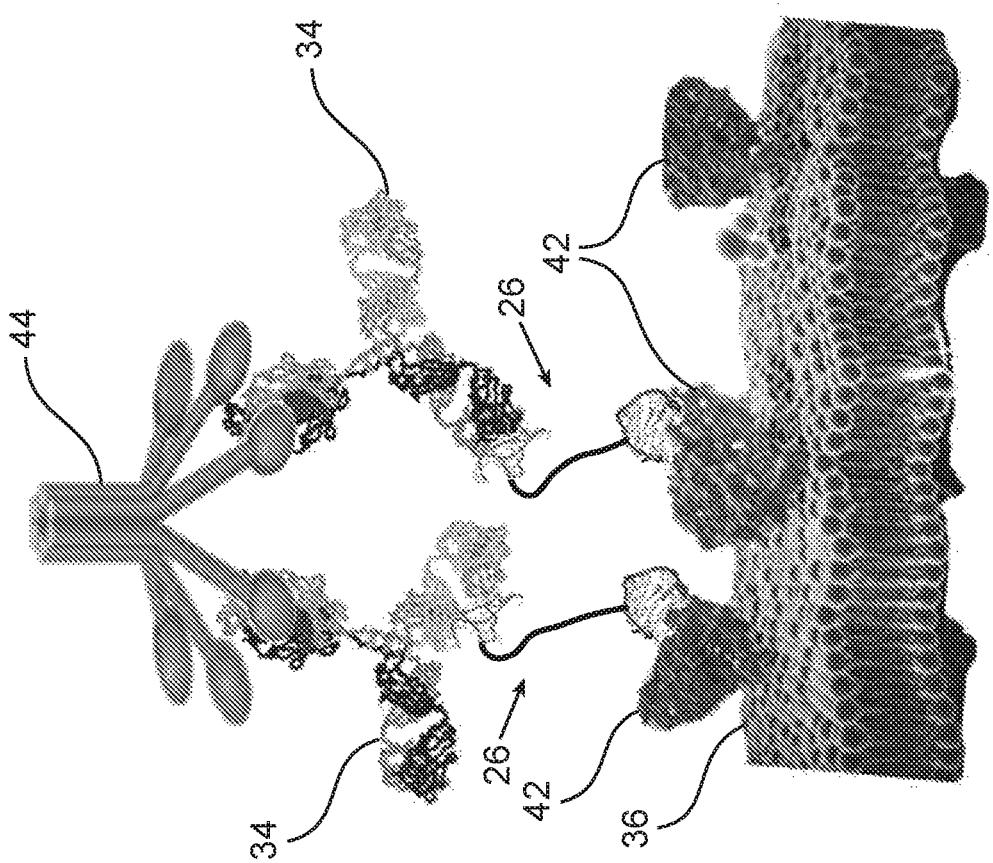
Figures 2, 2B:
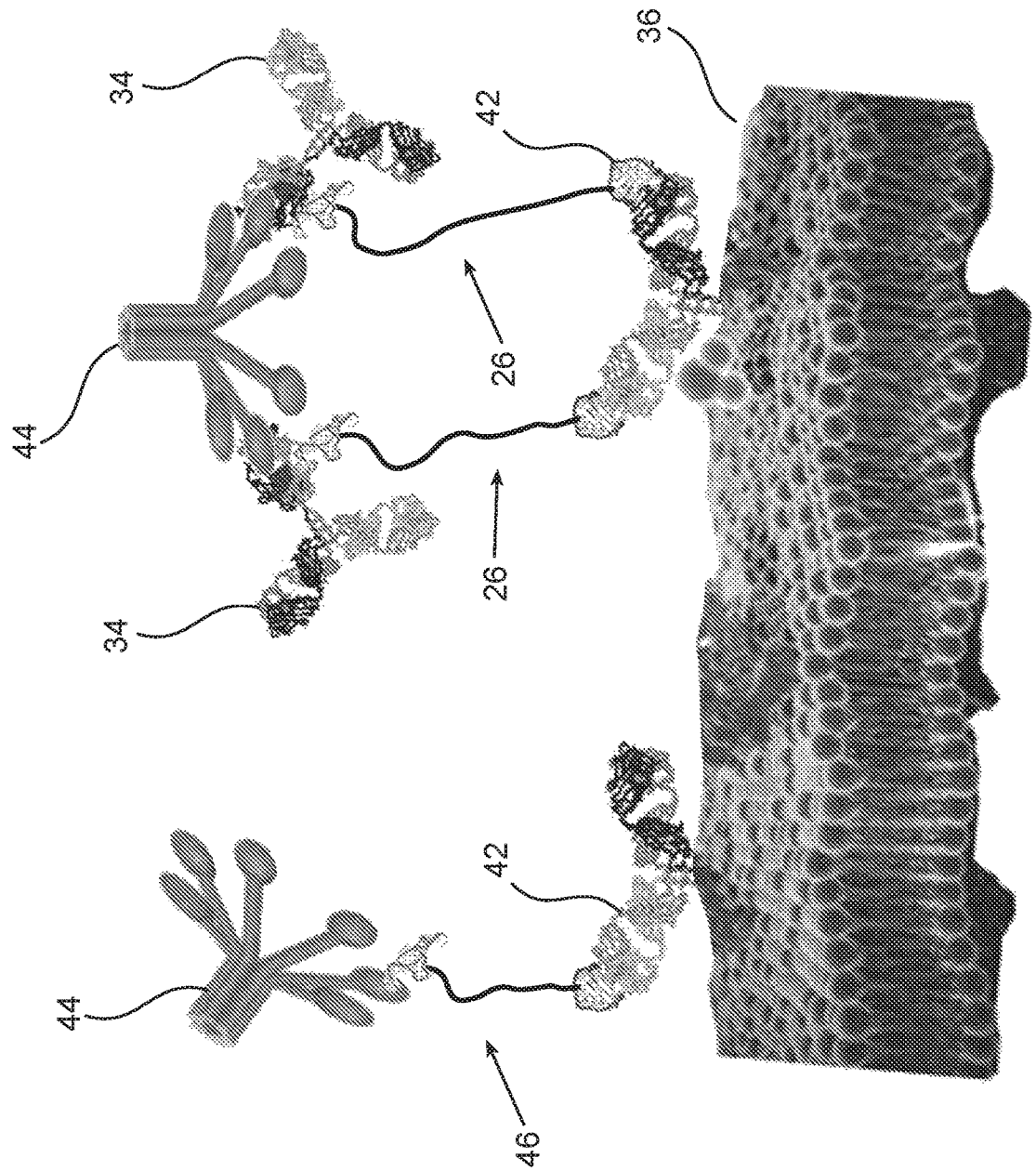

The "fused" aptamers can also be achieved by synthesis of what is called a Dual Aptamers Complex (DAC) particle (see FIG. 1D). The use of such DAC particles has the advantage of, inter alia: a) eliminating the needs for reagents and cross-linking procedure between the drug (such as an antibody) and the targeting element (i.e., biomarker-bonding portion); b) uses circulating natural serum elements (e.g., antibodies) as drugs, activating the body natural defense system, c) possess low immunity and relatively stable in the circulation and d) DAC particles are prepared chemically (e.g., solid state oligonucleotide synthesis), and therefore can easily be manufacture as a reagent for drug use, at low cost.

In some embodiments, the biomarker-bonding portions (the AptuBodies target binding element) are any ligand to a specific cell surface target, such as, but not limited to, oligopeptide (amino acid) aptamer strands, growth factors, small molecule and others, as long as that target binding element is relatively inerratic to the immune system.

Performing the Assay

A hypothesized mechanism of an embodiment of an AptuBody triggering the complement system is pictorially described in FIGS. 2A-1, 2A-2 and FIGS. 2B-1a, 2B-1b, and 2B-2. According to our preliminary results, complement activation will occur only when there will be high amount of biomarkers such as antigens on the cell surface. This avoids the death of normal body tissue expressing low level of the biomarker, in contrast to pathological cancer cells that over express the biomarker. Similarly, only memory B-cells expressing the aptamer-directed immunoglobin idiotope bind the AptuBodies and trigger the complement system. In the case of infectious diseases, complement activation occurs after the AptuBodies bind to the bacteria or virus surface, or to human cells expressing the "attacker" proteins on their surface.

This yields the destruction of the target membrane and death of the target cells, leading to reduce in tumor size or circulating tumor cells, the elimination of viruses, bacteria and infected cell from circulation, and to the destruction of autoimmune memory B-cells.

EXPERIMENTAL EXAMPLES

Abbreviations

Unless otherwise noted, all abbreviations herein have the accepted meaning known in the relevant art field. Such abbreviations include: IgG: Immune globulin G; h\m-IgG: human\mouse IgG; Ab: antibody; mAb: monoclonal antibodies; MIP: Molecularly imprinted polymer; MI: maleimide; PEG: polyethylene glycol; RBC: Red Blood Cell; sSMCC: Sulfo-SMCC (sulfosuccinimidyl 4-(N-maleimidomethyl)cyclohexane-1-carboxylate); PBS: Phosphate-buffered saline; DMSO: Dimethyl sulfoxide; DTT: Dithiothreitol; BSA: Bovine serum albumin; EDTA: Ethylenediaminetetraacetic acid; RPM: Round per minute; PDGF-BB: Platelet-Derived Growth Factor BB (*E. coli*); Lys: Lysozyme; MUC-1: Human Mucin-1 Protein; TNFa: Tumor necrosis factor a; HCV: Hepatitis C virus and HIV: human immunodeficiency virus All materials were purchased from known commercial sources and include: from Thermo Scientific, sSMCC; from Sigma-Aldrich: PBS, DMSO, DTT, h-IgG, h-IgG Fc fragment, EDTA, BSA, CaCl2, MgCl2, N-Acetyl-Cys, Tween-20, Lysozyme, MTT reagent, medium DMEM, from ABCAM: Hamster complement, Muc1 antigen, Muc1 Antibodies; from Invitrogen: Protein-A Sepharose beads; from GE: MiniTrap G-25; from Ella Biotech GmbH: oligonucleotide aptamer strands; from Prospec bio: PDGF-BB: Platelet-Derived Growth Factor BB; from ATTC: MCF7 breast adenocarcinoma cells, MDCK cells, EMEM medium; from Peproteck ASIA: Rabbit anti PDGFBB Abs, Recombinant Human PDGF-BB.

A. Example-1: Chemical Coupling of h-IgG/Fc or BSA to Human Red Blood Cells (RBC)

This experiment tests the ability of the complement system to induce hemolysis of red blood cells (RBC) which carries IgG or Fc fragment artificially attached to their cell membrane.

I. Materials:
1). RBC (from human donor) washed ×3 with PBS (Sigma-Aldrich, St. Louis, Mo., USA), re-suspend to 40% v:v. in PBS (Sigma Aldrich).
2). sSMCC cross linker (Thermo Scientific), 10 mg/ml in PBS 10% (Sigma Aldrich), DMSO (Sigma Aldrich)
3). DTT 1M (Sigma Aldrich)
4a). h-IgG (Sigma Aldrich), 4.8 mg/ml=0.032 umole/ml
4b). h-Fc (Sigma Aldrich), 3.2 mg/ml, 0.032 umole/ml
4c). BSA (Sigma Aldrich), 2.0 mg/ml=0.032 umole/ml
5). G-25 column (GE Healthcare Life Sciences, Marlborough, Mass., USA) of 10 ml (GE MiniTrap™ G-25)
6). PBS (Sigma Aldrich)
7). PBS/BSA 1 mg/ml (Sigma Aldrich)
8). PBS/EDTA 1 mM (Sigma Aldrich)
9). Complement buffer PBS/BSA(1 mg/ml)/CaCl2 (2 mM)/MgCl2 (2 mM) (all Sigma Aldrich)
10). Hamster complement (Abcham, Ab155111), 1:10 diluted in complement buffer.
11). Protein-A Sepharose beads (Invitrogen)
12). N-Acetyl-Cys (Sigma Aldrich)

II. Protein Activation:
1). Use a molar ratio of about 1:5 protein to sSMCC. Add 2.50 ul sSMCC (Freshly made) into 0.3 ml of protein preparation.
2). Incubate 90 minute at room temperature (RT).
4). Load onto dry G-25 column, and spin 2 min at 3500 RPM
5). Collect sup. Bring to 400 ul with PBS/EDTA 1 mM. Use immediately. Concentrations of Protein-Maleimide (MI) activated post G-25 column:
  h-IgG-MI—3.8 mg/ml, 8 nmol in 400 ul PBS
  Fc-MI—2.6 mg/ml, 8 nmol in 400 ul PBS
  BSA-MI—1.6 mg/ml, 8 nmol in 400 ul PBS III. RBC Reduction
1). To 1.0 ml RBC 40% v:v in PBS add 25 ul DTT of 1M
2). Incubated for 45 min. at RT
3). Wash Cells ×2 with 20 ml of PBS/BSA and ×3 with 20 ml of PBS.
4). Re-suspend cells in 1.0 ml PBS/EDTA 1 mM to 40% v:v, ($5 \times 10^9$ cells/ml)

IV. Protein/RBC Binding
1). Mix cells and proteins as directed in the table below:

| Tube | protein | Proteins amounts ul | (nmol) | RBC: ul ($7 \times 10^8$) |
|---|---|---|---|---|
| 1 | IgG | 300 | (6.0) | 150 |
| 2 | IgG | 60 | (1.2) | 150 |
| 3 | Fc | 300 | (6.0) | 150 |
| 4 | Fc | 60 | (1.2) | 150 |
| 5 | BSA | 300 | (6.0) | 150 |
| 6 | BSA | 60 | (1.2) | 150 |

2). Incubate 120 min at RT
3). Add N-Acetyl-Cys (Sigma)—100 ul 10 mg/ml in PBS (For MI blocking)
4). Incubate 120 min at RT
5). Wash Cells ×2 with 10 ml of PBS/BSA and ×2 with PBS.
6). Store at 4° C.

V. Part-I: Binding of Modified RBC to Protein-A/Sepharose Beads.

Figure 3A:
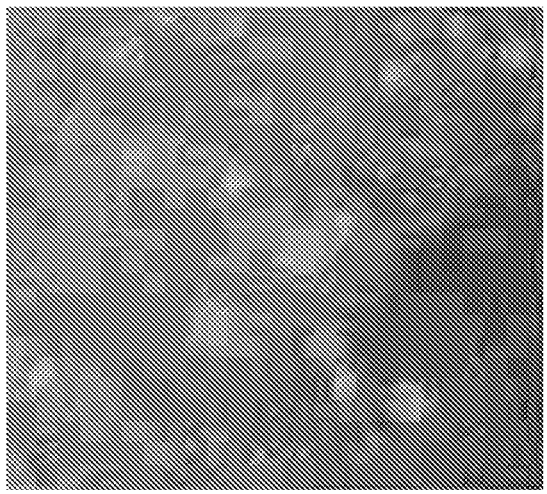
Figure 3B:
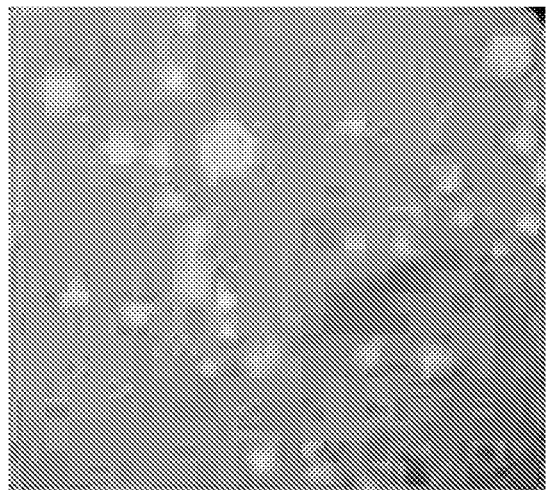
Figure 3C:
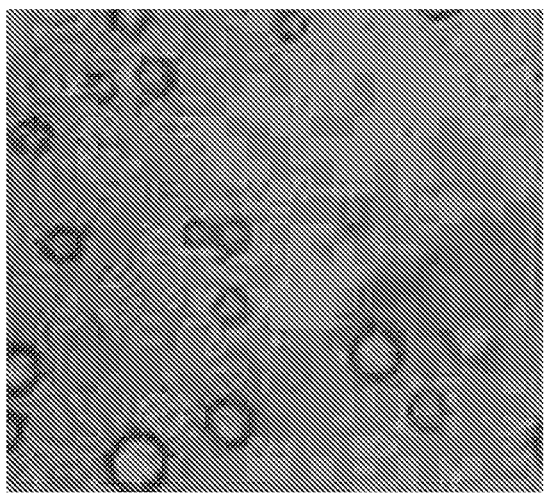
Figure 3D:
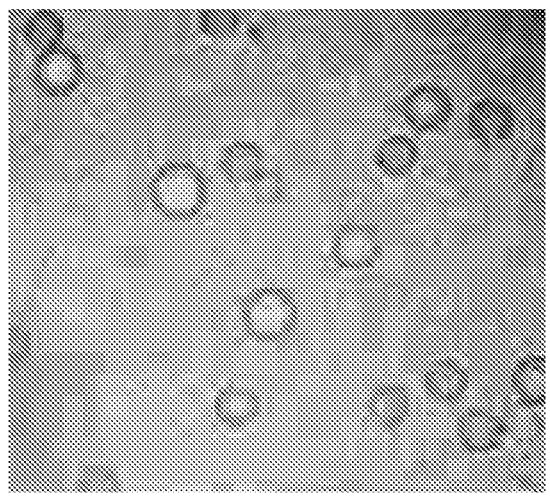

10 ul of stock Protein-A/Sepharose beads were added into 100 ul of 5% RBC in PBS and let 60 min at RT rolling. Samples were observed under the microscope (magnification ×40). Reproductions of these photographs are depicted in FIG. 3: FIG. 3A is of non-treated RBC, FIG. 3B is of BSA bound RBC, FIG. 3C is of h-IgG bound RBC. and FIG. 4D is of Fc-bound RBC.

Results and Discussion:

As can be seen, when about $5 \times 10^6$ activated IgG or Fc molecules (6 nm protein) were introduced per one activated RBC, a massive binding of the cells to the Protein-A Sepharose beads was observed. Less binding was observed when $10^6$ activated IgG or Fc molecules were added per cell (not shown). No binding of native RBC or BSA-coated RBC to the beads was observed.

Employing $I^{125}$ labeled IgG we have shown that under the above conditions, when about $5 \times 10^6$ activated IgG molecules were introduced per one activated RBC, about $5 \times 10^4$ IgG molecules were bound per one RBC (not shown). These results indicate that the chemically attached IgG or Fc can act as a bridge between the cells and the Protein-A beads, indicating that the cross linkers do not interfere with the Fc ability to bind to Protein-A.

VI. Part-II: Complement Induced Hemolysis of Modified RBC

1) In microtube, add 50 ul of Complement preparation into 100 ul of RBC 5% in complement buffer.
2). Incubate 60 min at 37° C.
3). Centrifuge cells 7000 RPM and collect sup.
4). Estimate hemolysis by the optical density of hemoglobin at 540 nm, in compare to 100% hemolysis by Tween-20.

Results and Discussion:

The results of this set of experiments are graphically depicted in FIG. 4 and show the complement-induced hemolysis of IgG/Fc coupled RBCs.

As can be seen, when 6 nm activated IgG or Fc (about $5 \times 10^6$ molecules) were introduced per one activated RBC, lysis of about 90% or 80% respectively was observed. Only 30%-40% RBC lysis was observed when 1.2 nm activated IgG or Fc (about $1 \times 10^6$ molecules) were added. About 5% RBC lysis was observed with native RBC or BSA-bound RBC.

These results indicate that IgG-Fc which chemically bound to RBC surface can bind the complement C1q and activate the complement cascade, leading to the RBC hemolysis. This C1q binding and activation is depended upon the IgG-Fc density (number of molecules on the cell surface), and not depended a conformational change of the IgG upon binding to the antigen. Our results (not shown) indicates that when about $1-2 \times 10^4$ IgG molecules were bound per one RBC, hemolysis of about 85% to 95% were obtained.

B. Example-2: AptuBodies Construction

I. Materials:
1. sSMCC cross linker (Thermo Scientific), 10 mg/ml in PBS 10% (Sigma Aldrich) DMSO (Sigma Aldrich) (23 nmole/ul)
2. DTT 1M (Sigma Aldrich)
3a). h-IgG (Sigma Aldrich), 3.7 mg/ml (24 pmol/ul)
3b). h-Fc (Sigma Aldrich), 2.4 mg/ml (24 pmol/ul)
3c). BSA (Sigma Aldrich), 1.5 mg/ml (24 pmol/ul)
4). G-25 column of 10 ml (GE MiniTrap™ G-25)
5). PBS (Sigma Aldrich)
6). PBS/BSA 1 mg/ml (Sigma Aldrich)
7). PBS/EDTA 1 mM (Sigma Aldrich)
8). PBS/EDTA 5 mM (Sigma Aldrich)
9). Anti-Lysozyme DNA aptamer (aLys) (23), 200 pmol/ul (Ella Biotech GmbH).

SEQ ID NO: 1 - Thiol-C$_{12}$-5'-ATCTA CGAAT TCATC

AGGGC TAAAG AGTGC AGAGT TACTT AG-3'

10). Anti-PDGF DNA aptamer (aPDGF) (24), 200 pmol/ul (Ella Biotech GmbH).

SEQ ID NO: 2 - Thiol-C$_{12}$-5'-GCGAT ACTCC ACAGG

CTACG GCACG TAGAG CATCA CCATG ATCCT G-3'

II. DNA Aptamers-Thiol Activation
1). 100 ul Aptamer (20 nm) were incubated in 100 mM DTT for 1 h at RT.
2). DNA-SH was loaded onto G-25 column saturated with PBS 5 mM EDTA and centrifuge for 2 min at 1000×g.
3). Aptamers-SH (aLys-SH and aPDGF-SH) were used imminently.

III. Protein-MI Formation
1). h-IgG, h-Fc or BSA, (500 ul 12 nm), were incubated with 10 ul of sSMCC in PBS/1 mM EDTA 10% DMSO, for 2 h at RT (20:1 m:m).
2). Protein-MI was loaded onto G-25 column saturated with PBS 5 mM EDTA and centrifuge for 2 min at 1000×g.
3). Protein-MI was used imminently.

IV. AptuBodies Construction
1). Protein-MI preparations, 500 ul (8 nmol) each, were mixed with 100 ul (16 nmol) of aptamers-SH preparations, at a molar ratio of 1:2.
2). Mixtures were incubated Over Night at RT.
3). Add N-Acetyl-Cys (Sigma)—10 ul 2 mg/ml in PBS (For MI blocking)
4). Store at 4° C. Aptubodies concentration is about 13 nmol/ul by protein:
    a). anti Lysozyme aptamer h-IGg AptuBodies (aLys-IgG)—2 mg/ml
    b). anti Lysozyme aptamer Fc AptuBodies (aLys-Fc)—1.3 mg/ml
    c). anti Lysozyme aptamer BSA AptuBodies (aLys-BSA)—0.8 mg/ml
    d). anti PDGF aptamer h-IGg AptuBodies (aPDGF-IgG)—2 mg/ml C. Example-3: AptuBodies Induced Complement Activation These experiments demonstrate the hemolysis of RBC induced by the complement system, being activated by AptuBodies directed against proteins that were artificially attached to the cell membrane. We have chosen the lysozyme antigen as a target, to be bound to the RBC surface. It is noted that the protein lysozyme has no enzymatic activity against RBC.

I. Materials:
1a). Lysozyme (Sigma Aldrich), 0.5 mg/ml=0.032 umole/ml
1b). BSA (Sigma Aldrich), 2.0 mg/ml=0.032 umole/ml
2a). anti Lysozyme aptamer h-IGg AptuBodies (aLys-IgG) from above
2b). anti Lysozyme aptamer Fc AptuBodies (aLys-Fc) from above
2c). anti Lysozyme aptamer BSA AptuBodies (aLys-BSA) from above
2d). anti PDGF aptamer h-IGg AptuBodies (aPDGF-IgG) from above
3). Rabbit anti lysozyme Abs (polyclonal, Abcham) 1 mg/ml
4). Complement buffer PBS/BSA(1 mg/ml)/CaCl2 (2 mM)/MgCl2 (2 mM) (all Sigma Aldrich)
All other materials are as describe in sample-1 at section A and in sample-2 at section B.

II. Lysozyme and BSA Coupling to RBC
Protein activation, human RBC reduction and Protein/RBC binding were performed as describe in sample-1 at section A, employing 6.0 nm and 0.6 nm of lysozyme and 6.0 nm of BSA.

III. Aptubodies Preparation
Aptubodies were prepared as described in sample-2 at section B.

IV. AptuBodies Induced Hemolysis of Lysozyme=RBC
Part-I: Agglutination of Modified RBC by AptuBodies
50 ul of 1:10 dilution of anti Lysozyme Ab or AptuBodies preparation were incubated with 50 ul of 5% modified RBC in PBS for 1 h at RT with gentle shaking. Samples were observed under the microscope (magnification ×40).

Figure 5C:
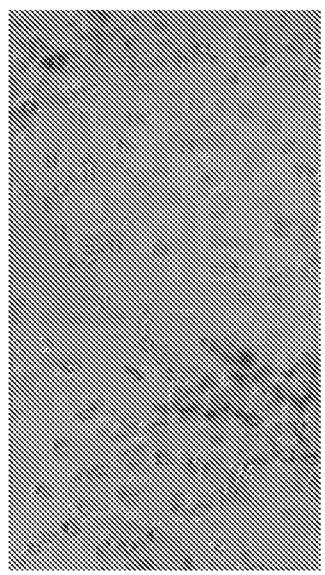
Figure 5F:
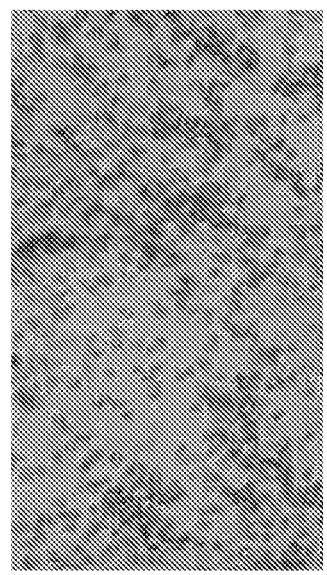
Figure 5B:
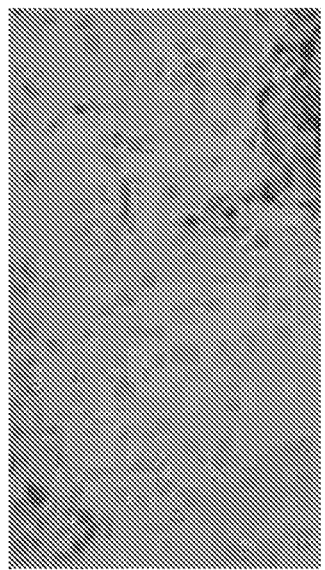
Figure 5E:
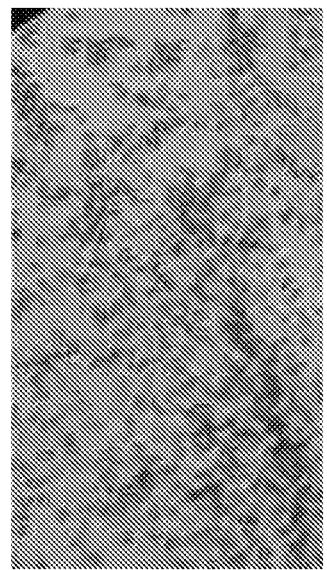
Figure 5A:
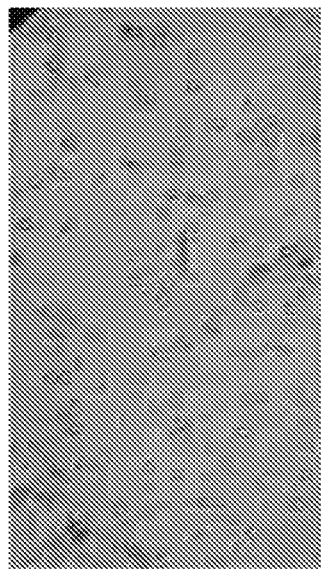
Figure 5D:
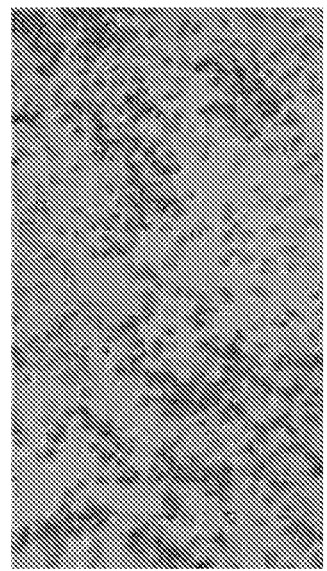

The results of this set of experiments are depicted in FIG. 5 that are reproductions of photographs showing that the AptuBodies described above induced agglutination of modified RBCs:

FIG. 5A non-modified cells with Lys-IgG Aptubodies;
FIG. 5B lysozyme-modified cells without a chemical entity according to the teachings herein;

FIG. 5C: BSA-modified cells with Lys-IgG Aptubodies;

FIG. 5D: lysozyme-modified cells with Anti-lysozyme-IgG;

FIG. 5E: lysozyme-modified cells with Lys-IgG Aptubodies; and

FIG. 5F: lysozyme-modified cells with Lys-Fc Aptubodies.

Results and Discussion

As can be seen, modification of the RBC by itself did not cause cell Agglutination, nor did the introducing of the AptuBodies to non-modified RBC or BSA modified RBC.

On the other hand, when anti Lysozyme Abs or aLys-AptuBodies (IgG or Fc base) were introduce to the RBC, cell Agglutination was observed. This indicates that under the conditions used, there were at least two aptamers per IgG/Fc molecule.

Part-2: aLys-IgG Induced Hemolysis of Modified RBC

1). To 40 ul of 20% RBC preparations in complement buffer add 20 ul aLys-IgG AptuBodies; Incubate for 1 hr. at room temperature.

2). Add 20 ul of Guinea Pig Complement or PBS and incubate for 20 minutes at 37° C.

3). Add 100 ul PBS, centrifuge the cells, collect the sup and read 540 nm.

Results and Discussion

The results of this set of experiments are graphically depicted in FIG. 6 and show the aLys-IgG described above induced hemolysis of Lysozyme-RBC.

These results demonstrate the ability of aLys-IgG AptuBodies and anti lysozyme Abs to lysozyme associate RBC, but not to BSA associate RBC and to trigger complement activation, leading to the RBC hemolysis. The RBC hemolysis was found to be depended on the amount of target antigen presence on the cells surface, showing more hemolysis when more antigen is presence on the cells surface. Similar results were obtained with native, un-modified, anti target (Lysozyme) Abs.

The results also indicate that the Aptamer part of the AptuBodies does not interfere with the Fc ability to bind and activate the complement system, similarly to native Abs.

Part-3: AptuBodies Specificity Test

All experimental methods were as describe in Part-2 above. The results of this set of experiments are graphically depicted in FIG. 7 that show how the aLys-IgG described above induced RBC hemolysis.

Results and Discussion

The results described in FIG. 7 further demonstrate the ability of antigen specific IgG/Fc AptuBodies to trigger complement activation, leading to its target RBC hemolysis.

D. Example-4: AptuBodies Induced Complement Killing of Cultured Cells Expressing the Muc1 Antigen We have shown that Aptubodies directed against cell surface antigen trigger complement activity and causes the hemolysis of RBC. To test whether Aptubodies may be directed in the same manner to pathological cell surface markers of living cells, we have chosen the MCF7 breast adenocarcinoma cells, which express the Muc1 antigen on their surface (ref. 25), an antigen that have a related Aptamer, describe in the literature (ref. 26). Working with these cells gives an advance in future studies as these cells are used in a mouse model for breast adenocarcinoma, employing anti Muc1 antibodies as a treatment (ref. 27). MDCK cells were used as a negative control cells. Estimation of MTT reagent incorporation was used as a tool for determinant the viability of the cell. In parallel, Methyl Blue staining was used as tool for determinant the cell membrane damaging and cell death.

I). Materials:

1). Anti-Muc1 DNA aptamer (aMuc) (Ella Biotech GmbH), 200 pmol/ul were a 1:1 mixture of 2 aptamers against the Muc1 antigen: 5TR1 and 5TRG2 (26):

5TR1:
SEQ ID NO: 3 - Thiol-$C_{12}$-5'-GAGAC AAGAA TAAAC
GCTCA AGAAG TGAAA ATGAC AGAAC ACAAC ATTCG ACAGG
AGGCT CACAA CAGGC-3'

5TRG2:
SEQ ID NO: 4 - Thiol-$C_{12}$-5'-GAGAC AAGAA TAAAC
GCTCA AGGCT ATAGC ACATG GGTAA AACGA CTTCG ACAGG
AGGCT CACAA CAGGC-3'

2a). anti Muc1 aptamer h-IGg AptuBodies (aMuc-IgG) 2 mg/ml by protein, from above.

2b). anti Muc1 aptamer Fc AptuBodies (aMuc-Fc) 1.3 mg/ml by protein, from above.

2c). anti Muc1 aptamer BSA AptuBodies (aMuc-BSA) 0.8 mg/ml by protein, from above.

2d). anti Lysozyme aptamer h-IGg AptuBodies (aLys-IgG) 2 mg/ml by protein, from above.

2e). anti Lysozyme aptamer Fc AptuBodies (aLys-Fc) 2 mg/ml by protein, from above.

3). Rabbit anti Muc1 Abs (polyclonal, Abcham ab1548) 0.2 mg/ml, from above.

4). MCF7 breast adenocarcinoma cells (ATCC® HTB-22™), grown in medium ATCC formulated EMEM [cat 30-2003] with insulin, in 96 well plates to 60%-80% confluences, at 37° C., 5% $CO_2$.

5). MDCK cells (ATCC CCL-34) cells, grown in medium DMEM (Sigma D5796), in 96 well plates to 60%-80% confluences, at 37° C., 5% $CO_2$.

6). MTT reagent (Sigma-Aldrich M5655)

All other materials, and AptuBodies construction, are as describe in sample-2 at section B and in sample-3 at section C.

II). AptuBodies Induced Cultured Cell Death

1) MCF7 cells and MDCK cells were grown in 96-well plate to 60-80% confluence, in their optimal growth medium and conditions.

2) Medium was removed, 50 ul of treatment mix 2.1-2.8 was applied in triplicates and cells were incubated 37° C. with 5% $CO_2$, for 2 h.

2.1) 10% PBS+10% complement in related buffer. (Control cells) 2.2) 10% PBS contains 1.0 ug (7 pmol) of Anti MUC1 antibodies+10% complement in related sera free medium.

2.3) 10% PBS contains 1.0 ug (7 pmol) of aMuc-IgG AptuBodies+10% complement in related sera free medium.

2.4) 10% PBS contains 1.5 ug (7 pmol) of aMuc-Fc AptuBodies+10% complement in related sera free medium.

2.5) 10% PBS contains 2.5 ug (7 pmol) of aMuc-BSA AptuBodies+10% complement in related sera free medium.

2.6) 10% PBS contains 1.0 ug (7 pmol) of aLys-IgG AptuBodies+10% complement in related sera free medium.

2.7) 10% PBS contains 1.5 ug (7 pmol) of aLys-Fc AptuBodies+10% complement in related sera free medium.

2.8) 10% PBS and 1% Tween20 in related buffer. (dead cells control).
3) After incubation 50 ul of 1 mg/ml MTT in PBS was added and incubated for 1 h at 37° C. with 5% $CO_2$.
5) Medium was removed, cells were washed with PBS and 100 ul of DMSO was added and mixed till complete dissolve of the dye.
6) The optical density of the dye was estimated at 493 nm.

The results below are summarizing several experiments

Results and Discussion

The results of this set of experiments are graphically depicted in FIG. 8 that show that the Aptubodies described above induced cultured cell death.

The results demonstrate that cultured cell death was induced by the complement system, being activated by AptuBodies directed against a target protein on the cells surface. No effect of the AptuBodies on control cells (MDCK) was observed.

Cell death was observed only when the AptuBodies contains IgG or Fc, but not when the aptamer was conjugated to BSA protein. Furthermore, Cell death was depended on the target related aptamer of the AptuBodies—aMuc1, and cell death was not observed when unrelated aptamer, aLys, were presence in the AptuBodies contract.

t-Test result (P values) showed significance as shown in FIG. 8.

E. Example-5a: DAC Particles Induced Complement Killing of Cultured Cells Expressing the Muc1 Antigen We have shown that Aptubodies, together with IgG/Fc can trigger complement activity and causes cultured cell death. To test whether the DAC particles can do the same, the following system was developed. MCF7 and MDCK cultured cells were chosen as target and control cells as describe above (example-4).

At the time that this experiment was conduct, the development of DAC that connect directly with Abs was not completed. For this reason, we have used a surrogate system, we interact an aptamer with the Ab via sandwich structure. We have both aptamer and Ab against the protein PDGFBB, this protein served as a non-covalent linker between the anti-PDGFBB-aptamer on one hand and the anti-PDGFBB-Ab on the other.

DAC particles were constructed to carry the anti MUC1aptamer—anti hPDGFBB aptamer. DAC particles composed of anti MUC1aptamer—anti hTNFa aptamer was used as negative control.

In order to promote IgG-DAC binding, h-PDGFBB antigen was incubated for 1 h at RT with affinity pure poly clonal Rabbit anti h-PDGFBB IgG at molar ratio of 20:1 of Ag to Ab. The high Ag excess meant to prevent the formation of immuno-complexes which can induce complement activity.

Estimation of MTT reagent incorporation was used as a tool for determinant the viability of the cell. In parallel, Methyl Blue staining was used as tool for determinant the cell membrane damaging and cell death.

I. Materials:
1). Anti-Muc1\anti-hPDGFBB or anti-hTNFa DAC particles (200 pmol/ul) were a 1:1 mixture of 2 DAC particles compos of 2 aptamers against the Muc1 antigen:
5TR1 and 5TRG2 (26)
Anti-hPDGFBB aptamer (Ella Biotech GmbH):

```
SEQ ID NO: 2 - 5'-GCGAT ACTCC ACAGG CTACG GCACG
TAGAG CATCA CCATG ATCCT G-3'
```

Anti-hTNFa aptamer, (Ella Biotech GmbH):

```
SEQ ID NO: 5 - 5'-TGGTG GATGG CGCAG TCGGC GACAA-3'
```

5TR1-PDGF DAC particle (Ella Biotech GmbH):

```
SEQ ID NO: 6 - 5'-GAGAC AAGAA TAAAC GCTCA AGAAG
TGAAA ATGAC AGAAC ACAAC ATTCG ACAGG AGGCT CACAA
CAGGC-SP18-GCGAT ACTCC ACAGG CTACG GCACG TAGAG
CATCA CCATG ATCCT G-3'
```

5TRG2-PDGF DAC particle (Ella Biotech GmbH):

```
SEQ ID NO: 7 - 5'-GAGAC AAGAA TAAAC GCTCA AGGCT
ATAGC ACATG GGTAA AACGA CTTCG ACAGG AGGCT CACAA
CAGGC-SP18-GCGAT ACTCC ACAGG CTACG GCACG TAGAG
CATCA CCATG ATCCT G-3'
```

Anti-hTNFa based DAC: as above, but anti-TNFa aptamer is located at the DAC 3'.
2). Rabbit anti Muc1 Abs (polyclonal, Abcham ab1548) 0.2 mg/ml
3). Rabbit anti PDGFBB Abs (polyclonal, PeproTech 500-P47) 0.2 mg/ml
4). Recombinant Human PDGF-BB (PeproTech 100-14B) 0.5 mg/ml
5). MCF7 breast adenocarcinoma cells (ATCC® HTB-22™), grown in medium ATCC formulated EMEM [cat 30-2003] with insulin, in 96 well plates to 60%-80% confluences, at 37° C., 5% $CO_2$.
6). MDCK cells (ATCC CCL-34) cells, grown in medium DMEM (Sigma D5796), in 96 well plates to 60%-80% confluences, at 37° C., 5% $CO_2$.
7). MTT reagent (Sigma-Aldrich M5655)
All other materials, and methods, are as describe above
II. AptuBodies Induced Cultured Cell Death
1) MCF7 cells and MDCK cells were grown in 96-well plate to 60-80% confluence, in their optimal growth medium and conditions.
2) Medium was removed, 75 ul of treatment mix 2.1-2.9 was applied in triplicates and cells were incubated 37° C. with 5% $CO_2$, for 2 h.
2.1) 10% PBS+10% complement in related sera free medium. (Control cells)
2.2) 10% PBS contains 1.5 ug (10 pmol) of Anti MUC1 antibodies+10% complement in related sera free medium.
2.3) 10% PBS contains 1.5 ug (10 pmol) of Anti h-PDGFBB antibodies+10% complement in related sera free medium.
2.4) 10% PBS contains 200 pmol of aMuc-aPDGF DAC particles+10% complement in related sera free medium.
2.5) 10% PBS contains 200 pmol of aMuc-aPDGF DAC particles and 1.5 ug (10 pmol) Anti h-PDGFBB antibodies+10% complement in related sera free medium.
2.6) 10% PBS contains 200 pmol of aMuc-aPDGF DAC particles and h-PDGFBB\Anti h-PDGFBB antibodies complex (1.5 ug Ab, 10 pmol)+10% complement in related sera free medium.
2.7) 10% PBS contains h-PDGFBB\Anti h-PDGFBB antibodies complex (1.5 ug Ab, 10 pmol)+10% complement in related sera free medium.

2.8) 10% PBS contains 200 pmol of aMuc-aTNFa DAC particles and h-PDGFBB\Anti h-PDGFBB antibodies complex (1.5 ug Ab, 10 pmol)+10% complement in related sera free medium.
2.9) 10% PBS and 1% Tween20 in related sera free medium. (dead cells control).
(The excess of OCA particles are needed as the PDGF Ag is in 20× then the Abs) 3) After incubation 75 ul of 1 mg/ml MTT in PBS was added and incubated for 1 h at 37° C. with 5% $CO_2$.
4) Medium was removed, cells were washed with PBS and 100 ul of DMSO was added and mixed till complete dissolve of the dye.
5) The optical density of the dye was estimated at 493 nm. The results below are summarizing several experiments
Results and Discussion
The results of this set of experiments are graphically depicted in FIG. 9 that show how the DAC particles described above induced cultured cell death.

The results demonstrate that cultured cell death was induced by the complement system, only after being activated by either:
a). anti-MUC1 Abs on MCF-7 cells—about 53%, but not on MDCK cells—about 7%.
b). Immune-complex elements (anti-PDGFBB\PDGFBB complex).
c). DAC particles directed against a target protein on the cells surface and PDGFBB, together with the anti-PDGFBB\PDGFBB complex.

The immune-complex elements prompted also death of the control MDCK cells (about 25% for MDCK cells and about 29% for MCF-7 cells), but increase in cell death was occurred only with MCF-7 cells, in the present of the MUC-PDGF DAC particles (about 48%), but not with the MUC-TNFa DAC particles.

No effect of the DAC particles or unrelated Abs was observed with both cell types. t-Test result (P values) showed significance as shown in FIG. 9.

Example-5b: DAC Particles Induced Complement Killing of Cultured Cells Expressing the Muc1 Antigen Using polyclonal Abs (Rabbit anti-PDGFBB) in the previous DAC experiment yield high background in killing both MCF7 and MDCK cells. This was probably due to complement activation by Immuno-Complexes, formed when more than one Ab was bound to same Antigen. This also effect and reduce the specific binding of the related aptamer to the Ab\Ag complex (steric effect and site competition).

To eliminate that effect, the same system was tested employing monoclonal Abs to PDGFBB.

DAC particles were constructed to carry the anti MUC1aptamer—anti hPDGFBB aptamer. DAC particles composed of anti MUC1aptamer—anti hTNFa aptamer was used as negative control. MCF7 was used as target cells and MDCK cells were used as negative control cells.

In order to promote IgG-DAC binding, h-PDGFBB antigen was incubated for 1 h at RT with mouse monoclonal anti h-PDGFBB IgG at molar ratio of 1:2, to maintain nearly no free Ag in the system (most of the Ag will bound to the IgG).

Estimation of MTT reagent incorporation was used as a tool for determinant the viability of the cell. In parallel, Methyl Blue staining was used as tool for determinant the cell membrane damaging and cell death.

I. Materials:
1). Anti-Muc1\anti-hPDGFBB or anti-hTNFa DAC particles (200 pmol/ul) were a 1:1 mixture of 2 DAC particles composed of 2 aptamers against the Muc1 antigen: 5TR1 and 5TRG2 (ref. 26)
Anti-hPDGFBB aptamer (Ella Biotech GmbH):

SEQ ID NO: 2 - 5'-GCGAT ACTCC ACAGG CTACG GCACG

TAGAG CATCA CCATG ATCCT G-3'

Anti-hTNFa aptamer (Ella Biotech GmbH):

SEQ ID NO: 5 - 5'-TGGTG GATGG CGCAG TCGGC GACAA-3'

5TR1-PDGF DAC particle (Ella Biotech GmbH):

SEQ ID NO: 6 - 5'-GAGAC AAGAA TAAAC GCTCA AGAAG

TGAAA ATGAC AGAAC ACAAC ATTCG ACAGG AGGCT CACAA

CAGGC-SP18-GCGAT ACTCC ACAGG CTACG GCACG TAGAG

CATCA CCATG ATCCT G-3'

5TRG2-PDGF DAC particle (Ella Biotech GmbH):

SEQ ID NO: 7 - 5'-GAGAC AAGAA TAAAC GCTCA AGGCT

ATAGC ACATG GGTAA AACGA CTTCG ACAGG AGGCT CACAA

CAGGC-SP18-GCGAT ACTCC ACAGG CTACG GCACG TAGAG

CATCA CCATG ATCCT G-3'

Anti-hTNFa based DAC: as above, but anti-TNFa aptamer is located at the DAC 3'.
2). Rabbit anti Muc1 Abs (polyclonal, Abcham ab1548) 0.2 mg/ml
3). Mouse Monoclonal (IgG1) to Human PDGF-BB (LsBio, LS-C38273) 0.5 mg/ml.
4). Mouse anti-Human PDGF-BB Monoclonal Antibody (MyBioSource, MBS690977) 100 ug.
5). Recombinant Human PDGF-BB (PeproTech 100-14B) 0.5 mg/ml
6). MCF7 breast adenocarcinoma cells (ATCC® HTB-22™), grown in medium ATCC formulated EMEM [cat 30-2003] with insulin, in 96 well plates to 60%-80% confluences, at 37° C., 5% $CO_2$.
7). MDCK cells (ATCC CCL-34) cells, grown in medium DMEM (Sigma D5796), in 96 well plates to 60%-80% confluences, at 37° C., 5% $CO_2$.
8). MTT reagent (Sigma-Aldrich M5655)
II. AptuBodies Induced Cultured Cell Death
1) MCF7 cells and MDCK cells were grown in 96-well plate to 60-80% confluence, in their optimal growth medium and conditions.
2) Medium was removed. 75 ul of treatment mix (see below) was applied in triplicates and cells were incubated 37° C. with 5% $CO_2$, for 2 h.
I) 10% PBS+10% complement in related sera free medium. (Control cells)
II) 10% PBS contains 1.5 ug (10 pmol) of Anti MUC1 antibodies+10% complement in related sera free medium.
III) 10% PBS contains 3.0 ug (20 pmol) of Anti h-PDGFBB antibodies LS-C38273+10% complement in related sera free medium.

IV) 10% PBS contains 3.0 ug (20 pmol) of Anti h-PDGFBB antibodies MBS690977+10% complement in related sera free medium.
V) 10% PBS contains 100 pmol of aMuc-aPDGF DAC particles+10% complement in related sera free medium.
VI) 10% PBS contains 100 pmol of aMuc-aPDGF DAC particles and 3.0 ug (20 pmol) Anti h-PDGFBB antibodies LS-C38273+10% complement in related sera free medium.
VII) 10% PBS contains 100 pmol of aMuc-aPDGF DAC particles and 3.0 ug (20 pmol) Anti h-PDGFBB antibodies MBS690977+10% complement in related sera free medium.
IIX) 10% PBS contains 100 pmol of aMuc-aPDGF DAC particles and h-PDGFBB\Anti h-PDGFBB antibodies LS-C38273 complex (50 pmol Abs and 25 pmol Ag)+10% complement in related sera free medium.
IX) 10% PBS contains 200 pmol of aMuc-aPDGF DAC particles and h-PDGFBB\Anti h-PDGFBB antibodies MBS690977complex (50 pmol Abs and 25 pmol Ag)+10% complement in related sera free medium.
X) 10% PBS contains h-PDGFBB\Anti h-PDGFBB antibodies LS-C38273 complex (50 pmol Abs and 25 pmol Ag)+10% complement in related sera free medium.
XI) 10% PBS contains h-PDGFBB\Anti h-PDGFBB antibodies MBS690977 complex (50 pmol Abs and 25 pmol Ag)+10% complement in related sera free medium.
XII) 10% PBS contains 200 pmol of aMuc-aTNFa DAC particles and h-PDGFBB\Anti h-PDGFBB antibodies LS-C38273 complex (50 pmol Abs and 25 pmol Ag)+10% complement in related sera free medium.
XIII) 10% PBS contains 200 pmol of aMuc-aTNFa DAC particles and h-PDGFBB\Anti h-PDGFBB antibodies MBS690977 complex (50 pmol Abs and 25 pmol Ag)+10% complement in related sera free medium.
XIV) 10% PBS and 1% Tween20 in related sera free medium. (dead cells control). 3) After incubation 75 ul of 1 mg/ml MTT in PBS was added and incubated for 1 h at 37° C. with 5% $CO_2$.
4) Medium was removed, cells were washed with PBS and 100 ul of DMSO was added and mixed till complete dissolve of the dye.
5) The optical density of the dye was estimated at 493 nm. Results were calculated as percent of 100% death (sample XIV).

Results and Discussion

All experiments perform with Anti h-PDGFBB antibodies LS-C38273 gave negative results. This might suggest that the anti PDGFBB aptamer sequence used bind the same or nearby epitope on the Ag surface.
The results of this set of experiments are graphically depicted in FIG. 10 that show how the DAC particles described above induced cultured cell death.
The results demonstrate that cultured cell death was induced by the complement system, only after being activated by either:
a). anti-NUC Abs on MCF-7 cells—about 63%, but not on MDCK cells—about 7%.
b). DAC particles directed against a target protein on the cells surface and PDGFBB, together with the anti-PDGFBB\PDGFBB complex.
No immune-complex was formed when mono-clonal Abs are used.
No effect was observed with specific and non-specific DAC particles by themselves on both cell types. No effect was observed also when non-specific DAC particles Were used together with the Ab/Ag complex or when unrelated Abs were used. t-Test result (P values) indicates the significance of the results.

This experiment proved that fully synthetic DAC particles can specifically induce cell-death of cells presenting cancerous bio-marker.

F. Example-6: The Use of AptuBodies for the Treatment of Autoimmune Disease and Allergies In autoimmune disease (and allergies), memory B-cell in the circulation is responsible for the secondary, rapid immune respond Eliminating this memory B-cell will lead to the "cure" of the disease. Amanda S. Lakamp and Miche M. Ouellette have described a ssDNA aptamer that binds selectively to the anti-FLAG M2 antibody and blocks its function (ref. 28). In their paper they suggest to use such "function blocking" technique, as a therapeutic method for patients with systemic lupus erythematosus, rheumatoid arthritis, and other autoimmune diseases. We suggest using such aptamers to construct AptuBodies for the elimination of memory B-cells related to the disease.

For example, The CCP positive rheumatoid arthritis is an autoimmune disease. These patients carry Abs against an antigen of their arthritis, which similar to the cyclic oligopeptide CCP (ref. 29). Being relatively small molecule, there is only few Abs antigen binding sites which directed against the numbers of IgG oligopeptide. Developing aptamers against these idiotypes, will lead to the construction of AptuBodies directed against memory B-cells presenting the related membrane immunoglobulin, leading to the killing of the B-cells and eliminating the disease.

Another example is Bullous Pemphigoid (BP). BP is chronic itchy blistering disorder found mainly in aged person, characterized by frequent occurring of tense blister and erythema. Target antigens of the autoantibodies in BP patient serum are BP180 and BP2301), also called BPAG1 and BPAG2 (30). Developing aptamers to the idiotopes of Abs directed against these antigens, will lead to the construction of AptuBodies directed against memory B-cells presenting these related membrane immunoglobulins, leading to the killing of the B-cells and relief/eliminating the disease.

Similarly, to above, selecting anti allergens IgG idiotypes and construing the related AptuBodies will lead to new therapeutic for allergies.

G. Example-7: The Use of AptuBodies for the Treatment of Infectious Diseases In many infectious diseases, mainly in viral diseases, the pathogens infect the host cells and multiply in them. As part of this route, the pathogen surface proteins are expressed on the host cell surface. These proteins can be used as target for Aptamers, introducing the AptuBodies as a useful tool that trigger complement induced infected cell death, fighting the disease.

One example for this approach is Hepatitis C virus (HCV), which attacks the liver cells, causing destruction of the liver. It has been found that HCV patients do not carry anti HCV Abs against their intrinsic virus's quasispecies (ref. 31). A conserved HCV-surface glycoprotein sequence and mAbs against that protein, which recognizing most virus subtypes has been reported (ref. 31). Another example is the expression of the HIV gp70 on the surface of infected cells. Aptamers for the HIV gp70 and for the HCV surface proteins has been repotted (ref. 32).

H. Example-8: The Use of AptuBodies as Passive Immunity

Passive immunity is the transition of active immunity in the form of ready-made antibodies.

AptuBodies can be widely used as Passive immunity, having target specific aptamers for specific binding the AptuBodies, and h-IgG or h-Fc for triggering the immune and particularly the complement system, eliminating the pathogen. The pathogen can be, but not limited to, Bacteria, Virus, and others. Aptamers directed against surface elements of such invaders were described (ref. 20, 33).

The low immunity and low cost of the DAC particles place them as a useful tool for Passive immunity.

I. Example-9: In-Vivo Experiment with DAC AptuBodies (Prophetic Example)

This experiment evaluates the potential anti-tumor activity of AptuBodies and compare it with other treatments in the mouse MCF-7 metastatic breast tumor model in ICR-SCID mice
Species & Gender:
  C.B-17/IcrHsd-Prkdcscid mice, female, 10-11 weeks of age at tumor induction.
Group Size:
  n=7
No. of Groups:
  1 Vehicle Control group; 5 Test Items groups: (i) Anti-MUC1 Ab. (ii) Non-specific Ab. (iii) Anti-MUC1 Aptubody (iv) Non-specific Aptubody (v) Aptamer. Total n=42 Acclimation:
  At least 5 days.
Tumor Induction:
  By a single IV injection of $1\times10^5$ cells/animal at a dose volume of maximum 200 □l/Animal on day 0. On the day of tumor cell injection animals will be subjected to subcutaneous implantation of $17_\beta$-Estradiol pellet under general anesthesia.
Treatment:
  The various Test Items are injected 1-day post tumor cells injection, by IV injection at a volume dosage of maximum 10 ml/kg
Examinations:
  Body Weight and Detailed Clinical Signs—Once a week. Daily cage side observations and survival check.
Study Period:
  60 days
Study Termination:
  Full detailed macroscopic examination of moribund, dead and all survivors, including collection of abnormalities (i.e. suspected metastases). All collected tumors/organs/tissues will be fixed in 4% formaldehyde solution for histopathological evaluation.
Results:
  The effect of the treatments will be evaluated by body weight, survival, tumor size and pathology as well as metastasis.

Unless otherwise defined, all technical and scientific terms used herein have the same meaning as commonly understood by one of ordinary skill in the art to which the invention pertains. In case of conflict, the specification, including definitions, takes precedence.

As used herein, the terms "comprising", "including", "having" and grammatical variants thereof are to be taken as specifying the stated features, integers, steps or components but do not preclude the addition of one or more additional features, integers, steps, components or groups thereof.

As used herein, the indefinite articles "a" and "an" mean "at least one" or "one or more" unless the context clearly dictates otherwise.

As used herein, when a numerical value is preceded by the term "about", the term "about" is intended to indicate +/−10%.

As used herein, a phrase in the form "A and/or B" means a selection from the group consisting of (A), (B) or (A and B). As used herein, a phrase in the form "at least one of A, B and C" means a selection from the group consisting of (A), (B), (C), (A and B), (A and C), (B and C) or (A and B and C).

In some instances herein, the term "aptamer" is used as a synonym for "oligonucleotide aptamer strand".

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

REFERENCES

1. Parkin J, Cohen B "An overview of the immune system" in Lancet 2001, 2, 357 (9270), 1777-1789.
2. "Autoimmune Diseases, Acute and Complex Situations" in Khamashta, Munther A.; Ramos-Casals, Manuel (Ed), 1st Edition., 2011, XII, 416 p.
3. Sridhar Rao P N., "B cell activation and Humoral Immunity" http://www.microrao.com/micronotes/pg/humoral_immunity.pdf
4. Tangye S G, Tarlinton D M in "Memory B cells: Effectors of long-lived immune Responses" in Eur J Immunol 2009, 39, 2065-2075.
5. Pandey S "Hybridoma technology for production of monoclonal antibodies" in Int J Pharma Sci Rev and Res 2010, 1(2), 88-94.
6. Queen C, Schneider W P, Selick H E, Payne P W, Landolfi N F, Duncan J F, Avdalovic N M, Levitt M, Junghans R P, Waldmann T A. "A humanized antibody that binds to the interleukin 2 receptor" Proc Natl Acad Sci USA. 1989, 86 (24), 10029-10033.
7. Harding F A, Stickler M M, Razo J, DuBridge R B "The immunogenicity of humanized and fully human antibodies" in MAbs 2010, 2(3), 256-265.
8. Scott A M, Wolchok J D, Old L J "Antibody therapy of cancer" in Nature Reviews Cancer 2012, 12, 278-287.
9. Duerst R E, Ryan D H and Frantz C N "Variables Affecting the Killing of Cultured Human Neuroblastoma Cells with Monoclonal Antibody and Complement" in Cancer Res 1986, 46, 3420-3425.

10. Hakulinen J, Meri S "Complement-mediated killing of microtumors In Vitro" Am J Pathol 1998, 153(3), 845-855.
11. Goronzy J J, Weyand C M "The innate and adaptive immune systems" in Goldman L, Ausiello D, eds. Cecil Medicine. 23rd ed. Philadelphia, Pa.: Saunders Elsevier; 2007: chapter 42.
12. Grimm D, Bauer J, Pietsch J, Infanger M, Eucker J, Eilles C, Schoenberger J., "Diagnostic and therapeutic use of membrane proteins in cancer cells" Curr Med Chem 2011, 18(2), 176-190.
13. Nathan O. Stitziel, Brenton G. Mar, Jie Liang and Carol A. Westbrook "Membrane-Associated and Secreted Genes in Breast Cancer" Cancer Research 2004, 64, 8682-8687.
14. Rettig W J, Old U "Immunogenetics of human cell surface differentiation" in Annu Rev Immunol 1989, 7, 481-511.
15. Weiner L M, Surana R., Wang S "Monoclonal antibodies: versatile platforms for cancer immunotherapy" in Nature Rev Immunol 2010, 10, 317-327.
16. Qu Z, Griffiths G L, Wegener W A, Chang C H, Govindan S V, Horak I D, Hansen H J, Goldenberg D M "Development of humanized antibodies as cancer therapeutics" Methods 2005, 36, 84-95.
17. James W "Aptamers" in Encyclopedia of Analytical Chemistry. R.A. Meyers (Ed.) pp. 4848-4871, John Wiley & Sons Ltd, Chichester, 2000.
18. Pai S S, Ellington A D "Using RNA aptamers and the proximity ligation assay for the detection of cell surface antigens" in Methods Mol Biol 2009, 504, 385-98.
19. Cibiel A, Dupont D M, Ducongé F "Methods To Identify Aptamers against Cell Surface Biomarkers" in Pharmaceuticals 2011, 4, 1216-1235
20. Tombelli S, Minunni M, Mascini M "Aptamers-based assays for diagnostics, environmental and food analysis" in Biomol Eng 2007 24, 191-200. Epub 2007 Mar. 23. Review.
21. Tan W, Wang H, Chen Y, Zhang X, Zhu H, Yang C, Yang R "Molecular aptamers for drug delivery" in Trends Biotechnol 2011, 29(12), 634-640.
22. Ferreira C S M, Cheung M C, Missailidis S, Bisland S, GariépyJ "Phototoxic aptamers selectively enter and kill epithelial cancer cells" Nucleic Acids Res 2009, 37(3), 866-876.
23. Tran D T, Janssen K P F, Pollet J, Lammertyn E, Anné J, Van Schepdael A, Lammertyn J "Selection and Characterization of DNA Aptamers for Egg White Lysozyme" Molecules 2010, 15, 1127-1140.
24. Huang Y, Nie X M, Gan S L, Jiang J H, Shen G L, Yu R Q "Electrochemical immunosensor of platelet-derived growth factor with aptamer-primed polymerase amplification" in Analytical Biochemistry 2008, 382, 16-22.
25. Brayman M, Thathiah A, Carson D D "MUC1: a multifunctional cell surface component of reproductive tissue epithelia" in Reprod Biol Endocrinol 2004, 2, 4.
26. Ferreira C S M, Cheung M C, Missailidis S, Bisland S, Gariépy J "Phototoxic aptamers selectively enter and kill epithelial cancer cells" Nucleic Acids Res 2009, 37(3), 866-876.
27. Rowse G J, Tempero R M, VanLith M L, Hollingsworth M A, Gendler S J "Tolerance and Immunity to MUC1 in a Human MUC1 Transgenic Murine Model" Cancer Res 1998, 58, 315-321.
28. Lakamp A S, Ouellette M M "A ssDNA Aptamer That Blocks the Function of the Anti-FLAG M2 Antibody" J Nucl Acids 2011, Art I D 720798.
29. Silveira I G, Burlingame R W, von Mühlen C A, Bender A L, Staub H L "Anti-CCP antibodies have more diagnostic impact than rheumatoid factor (R F) in a population tested for RF" in Clin Rheumatol 2007, 26(11),1883-1889.
30. Liu Z "Are Anti-BP180 IgG1 or IgG4 Autoantibodies Pathogenic?" in J Invest Dermatol 119(5), 989-990.
31. Hanuka N, Sikuler E, Tovbin D, Neville L, Nussbaum O, Mostoslaysky M, Orgel M, Yaari A, Manor S, Dagan S, Hilzenrat N, Shemer-Avni Y "Hepatitis C virus infection in dialysis and chronic liver patients: Viraemia dependent anti-E2-antibody response" J Med Virol 2004, 73(4), 529-535.
32. Zhou J, Li H, Zhang J, Piotr S, Rossi J "Development of cell-type specific anti-HIV gp120 aptamers for siRNA delivery" in J Vis Exp 2011, 23(52), 2954.
33. Bruno J G "A Review of Therapeutic Aptamer Conjugates with Emphasis on New Approaches" in Pharmaceuticals 2013, 6, 340-357.

The invention claimed is:

1. An artificial chemical entity, comprising:
   a. a biomarker-bonding portion comprising a DNA oligonucleotide aptamer that selectively binds to Muc1 antigen; and
   b. an immune-response trigger comprising IgG or an Fc region of IgG;
   wherein under in vivo conditions binding of the biomarker-bonding portion to Muc1 antigen on a cell positions the IgG Fc region in proximity of said Muc1 antigen.

2. The chemical entity of claim 1, wherein said biomarker-bonding portion comprises a Muc1-binding oligonucleotide aptamer selected from the group consisting of an oligonucleotide set forth herein as SEQ ID NO: 3 and SEQ ID NO: 4.

3. The chemical entity of claim 1, wherein said biomarker-bonding portion is bonded to said immune-response trigger with a non-covalent associative bond.

4. The chemical entity of claim 1, wherein said biomarker-bonding portion is directly covalently bonded with a covalent bond to said immune-response trigger.

5. The chemical entity of claim 4, wherein said covalent bond is through a residue of a reactive group selected from the group consisting of NH2, SH, COOH, PO4, tosyl, thiol, a photo-reactive group, a click-chemistry group and a member of an affinity couple.

6. The chemical entity of claim 1, further comprising a linker bonded to said biomarker-bonding portion.

7. The chemical entity of claim 6, wherein said immune-response trigger is bonded to said linker.

8. The chemical entity of claim 6, wherein said linker is a chain comprising individual monomer residues selected from the group consisting of monosaccharide residues, nucleotide residues and combinations thereof.

9. A pharmaceutical composition comprising:
   the chemical entity of claim 1; and
   a pharmaceutically-acceptable carrier.

10. A method of treatment of breast cancer, comprising administering a pharmaceutically-effective amount of the chemical entity of claim 1 to a subject in need thereof.

* * * * *